US010293128B2

(12) United States Patent
Wolf et al.

(10) Patent No.: US 10,293,128 B2
(45) Date of Patent: May 21, 2019

(54) SYSTEM AND METHOD FOR EMERGENCY APNEIC OXYGENATION

(71) Applicants: Jeffrey S. Wolf, Owings Mills, MD (US); Aldo T. Iacono, Cockeysville, MD (US)

(72) Inventors: Jeffrey S. Wolf, Owings Mills, MD (US); Aldo T. Iacono, Cockeysville, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 976 days.

(21) Appl. No.: 14/602,991

(22) Filed: Jan. 22, 2015

(65) Prior Publication Data
US 2015/0182716 A1 Jul. 2, 2015

Related U.S. Application Data

(63) Continuation-in-part of application No. PCT/US2013/051739, filed on Jul. 23, 2013.
(Continued)

(51) Int. Cl.
*A61M 16/00* (2006.01)
*A61M 16/04* (2006.01)
(Continued)

(52) U.S. Cl.
CPC ..... *A61M 16/0472* (2013.01); *A61B 17/3415* (2013.01); *A61M 16/047* (2013.01);
(Continued)

(58) Field of Classification Search
CPC .......... A61M 16/0472; A61M 16/0486; A61M 16/0463; A61M 16/047; A61M 25/00; A61B 17/3415
See application file for complete search history.

(56) References Cited

U.S. PATENT DOCUMENTS 3,788,326 A * 1/1974 Jacobs .................. A61M 16/00
128/207.15
4,231,365 A * 11/1980 Scarberry ............. A61M 16/04
128/207.15
(Continued)

FOREIGN PATENT DOCUMENTS

DE 3335715 4/1985
DE 3335715 A1 4/1985
(Continued)

OTHER PUBLICATIONS

EPO, Extended Search Report, European Patent Application No. 13823262.4, dated Feb. 24, 2016, 5 pages.
(Continued)

*Primary Examiner* — Steven O Douglas
(74) *Attorney, Agent, or Firm* — Beusse Wolter Sanks & Maire, PLLC; Eugene Molinelli

(57) ABSTRACT

Techniques for emergency apneic oxygenation include a cannula having a longitudinal inner passage with an inner diameter. A distal portion has a first outer diameter greater than the inner diameter, and is made of shape memory material shaped to bend in a first direction along the inner passage. A cannula base has a second outer diameter greater than the first outer diameter. A distance from a distal end of the cannula to a proximal end of the distal portion of the cannula is less than a distance from a surface of a throat of a subject to a distal surface of an airway of the subject. The inner passage is configured to pass a catheter connected at a proximal end to an oxygen source. In various embodiments, the cannula is used with a trocar and, optionally, a system base, or supplied in a kit with a catheter.

18 Claims, 20 Drawing Sheets

Related U.S. Application Data

(60) Provisional application No. 61/930,043, filed on Jan. 22, 2014, provisional application No. 61/674,414, filed on Jul. 23, 2012.

(51) Int. Cl.
*A61B 17/34* (2006.01)
*A61M 25/00* (2006.01)

(52) U.S. Cl.
CPC .... *A61M 16/0463* (2013.01); *A61M 16/0486* (2014.02); *A61M 25/00* (2013.01)

(56) References Cited

U.S. PATENT DOCUMENTS

| | | | |
|---|---|---|---|
| 4,331,138 A * | 5/1982 | Jessen | A61M 16/0472 |
| | | | 128/200.26 |
| 4,643,188 A | 2/1987 | Weiss | |
| 4,677,978 A | 7/1987 | Melker | |
| 4,869,718 A | 9/1989 | Brader | |
| 4,978,334 A * | 12/1990 | Toye | A61B 17/3421 |
| | | | 604/164.1 |
| 5,251,616 A | 10/1993 | Desch | |
| 5,967,143 A | 10/1999 | Klappenberger | |
| 6,706,017 B1 * | 3/2004 | Dulguerov | A61M 16/0472 |
| | | | 128/207.29 |
| 6,742,519 B2 * | 6/2004 | Turnbull | A61M 16/0472 |
| | | | 128/207.14 |
| 7,169,129 B2 * | 1/2007 | Gooden | A61M 16/0472 |
| | | | 128/207.29 |
| 7,267,124 B1 * | 9/2007 | Roberson, Jr. | A61M 16/0472 |
| | | | 128/207.29 |
| 7,341,061 B2 | 3/2008 | Wood | |
| 7,373,939 B1 * | 5/2008 | DuBois | A61M 16/0472 |
| | | | 128/200.26 |
| 8,356,598 B2 * | 1/2013 | Rumsey | A61M 16/0472 |
| | | | 128/207.29 |
| 2004/0210114 A1 | 10/2004 | Simon | |
| 2005/0039755 A1 | 2/2005 | Gooden | |
| 2005/0065496 A1 * | 3/2005 | Simon | A61B 1/247 |
| | | | 604/500 |
| 2006/0015131 A1 | 1/2006 | Kierce et al. | |
| 2008/0251083 A1 | 10/2008 | Fetcenko et al. | |
| 2009/0229614 A1 | 9/2009 | Bateman | |
| 2009/0260625 A1 | 10/2009 | Wondka | |
| 2011/0041854 A1 | 2/2011 | Rasor et al. | |
| 2012/0145147 A1 * | 6/2012 | Freitag | A61M 16/0468 |
| | | | 128/200.26 |
| 2013/0041345 A1 * | 2/2013 | Kilcoin | A61B 17/3472 |
| | | | 604/506 |

FOREIGN PATENT DOCUMENTS

| | | |
|---|---|---|
| DE | 102009030313 A1 | 12/2010 |
| EP | 0 122 901 A | 10/1984 |
| EP | 0 480 653 A1 | 4/1992 |
| EP | 1 393 768 A1 | 3/2004 |
| JP | 2013074987 A | 4/2013 |
| WO | 2003075979 | 9/2003 |
| WO | 2009/149555 A1 | 12/2009 |
| WO | 2014018565 | 1/2014 |

OTHER PUBLICATIONS

ISA/US, "International Search Report & Written Opinion for the corresponding PCT application PCT/US2015/012465", dated May 1, 2015, pp. 1-7.

EPO: Partial Supplementary Search Report, European Patent Application No. 15740996.2, dated Aug. 22, 2017, 12 pages.

EPO: Extended Search Report, European Patent Application No. 15740996.2, dated Nov. 27, 2017, 9 pages.

ISA/US, "International Search Report & Written Opinion for the corresponding PCT application PCT/US2013/051739", dated Oct. 24, 2013, pp. 1-19.

\* cited by examiner

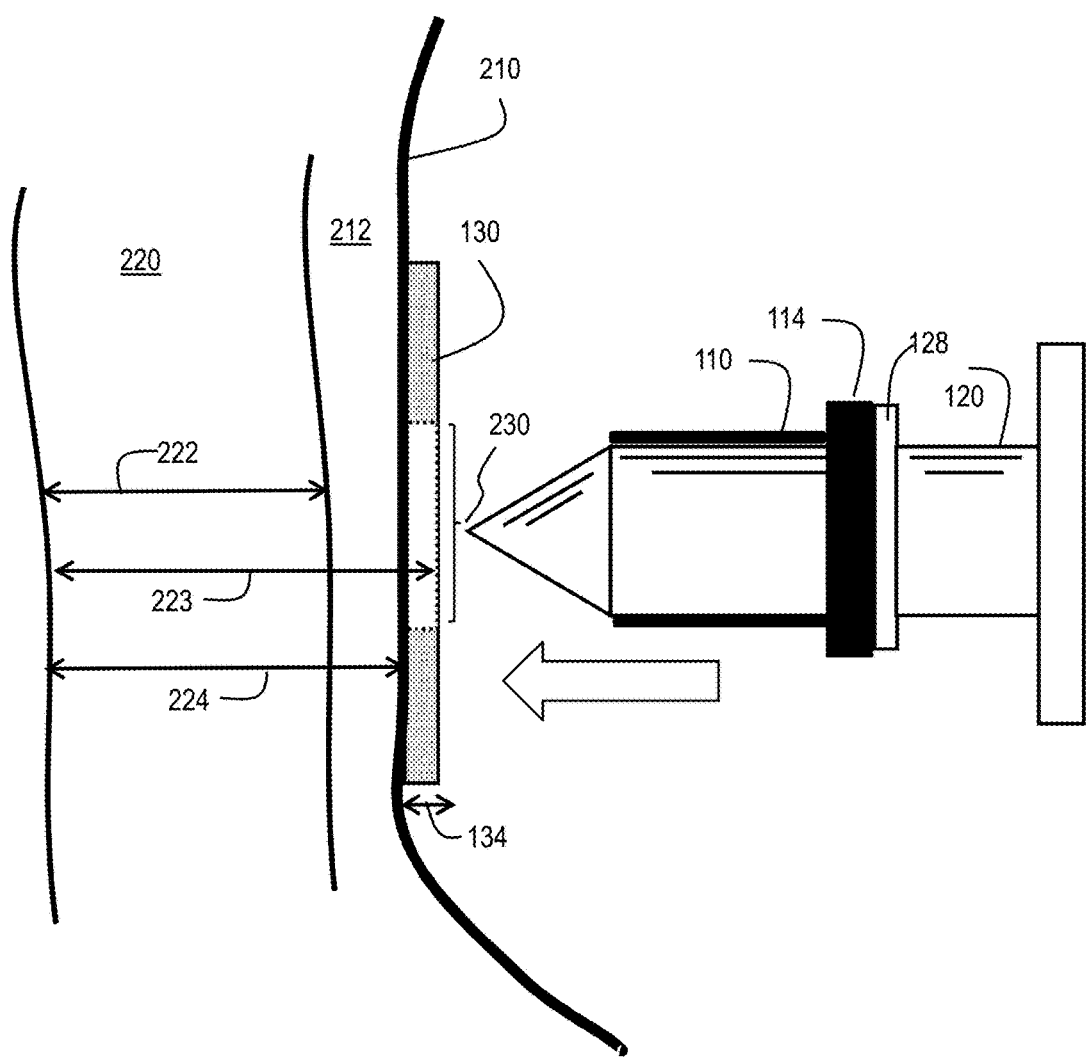

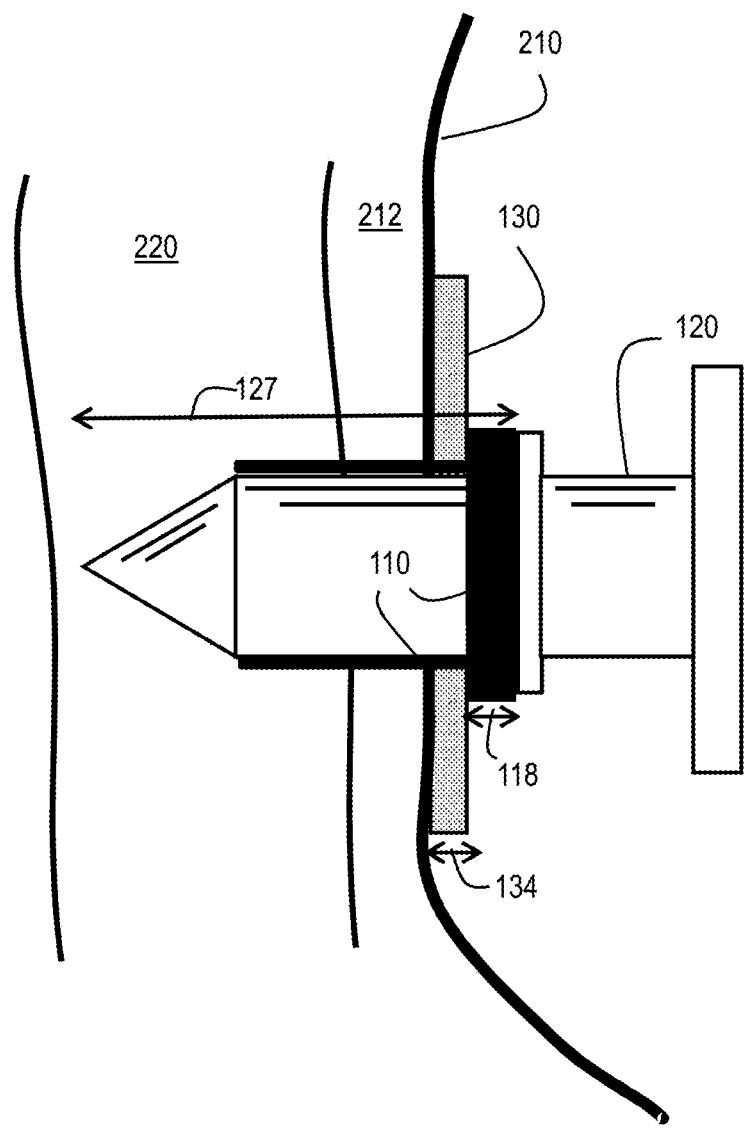

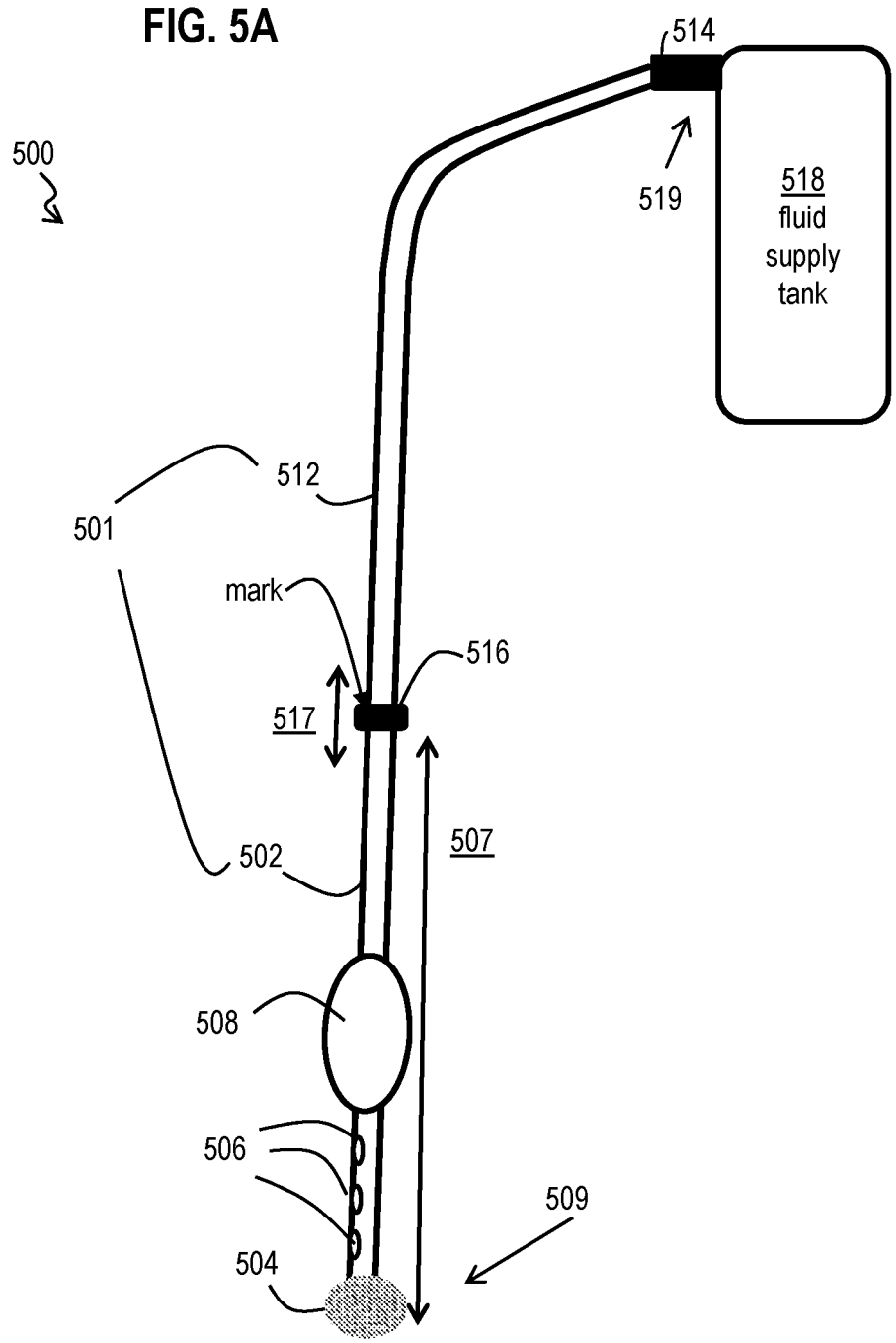

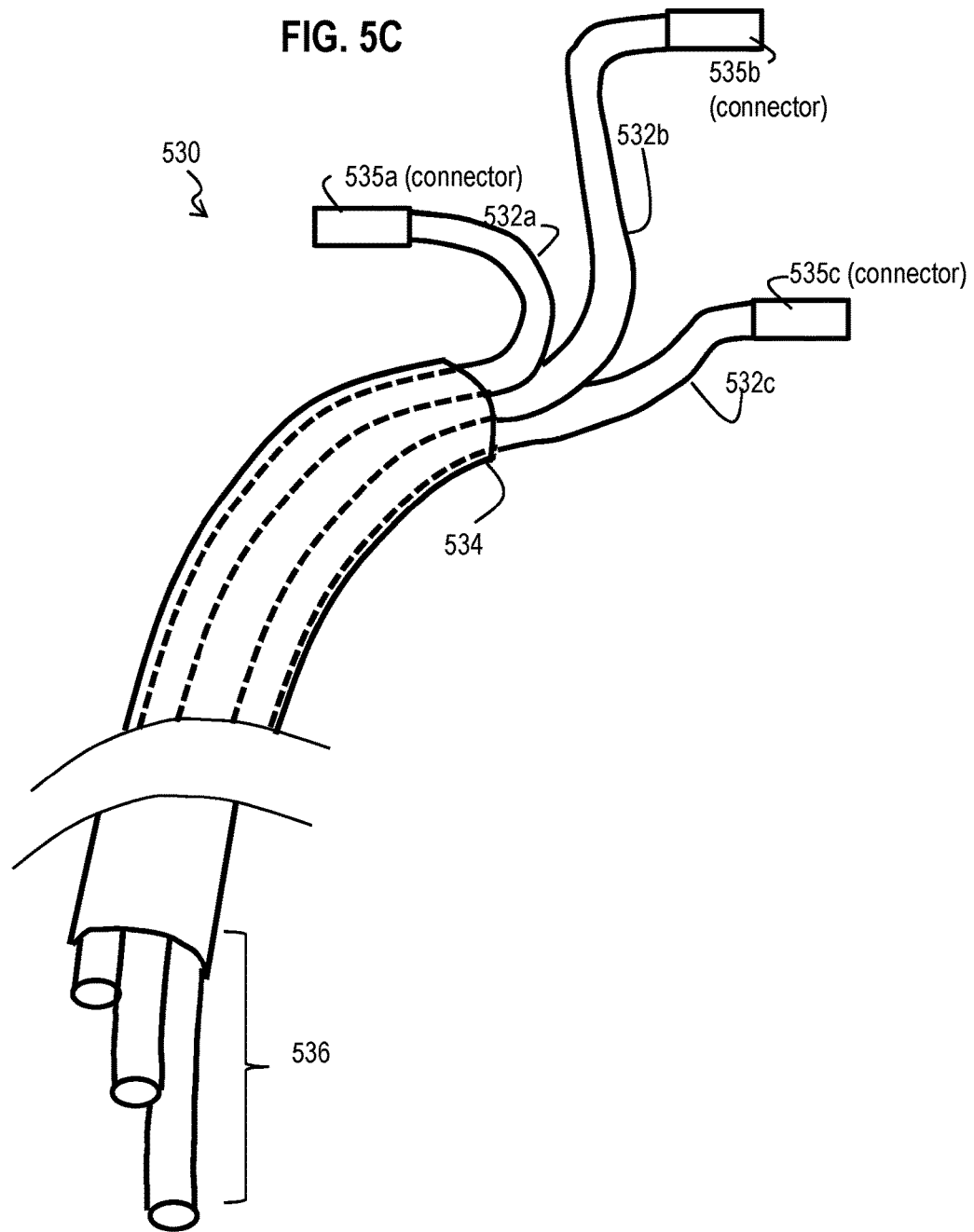

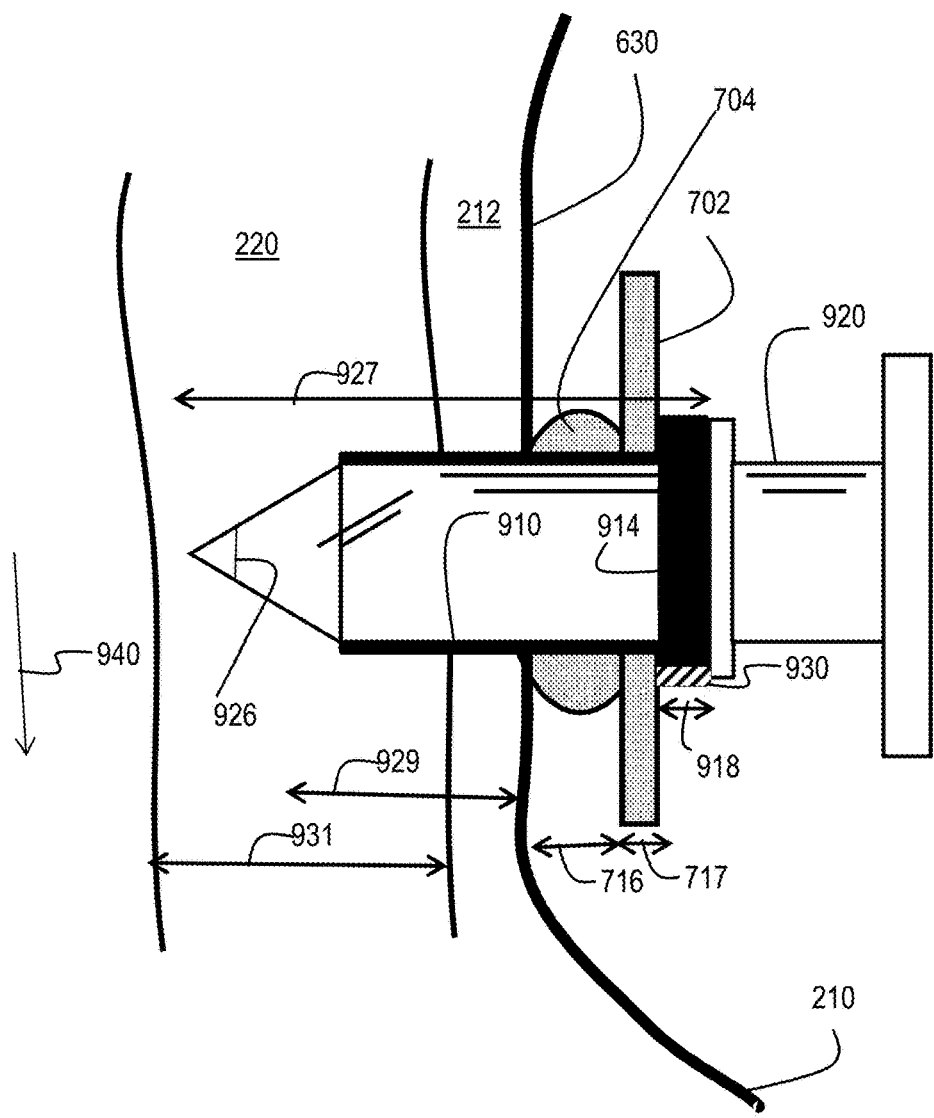

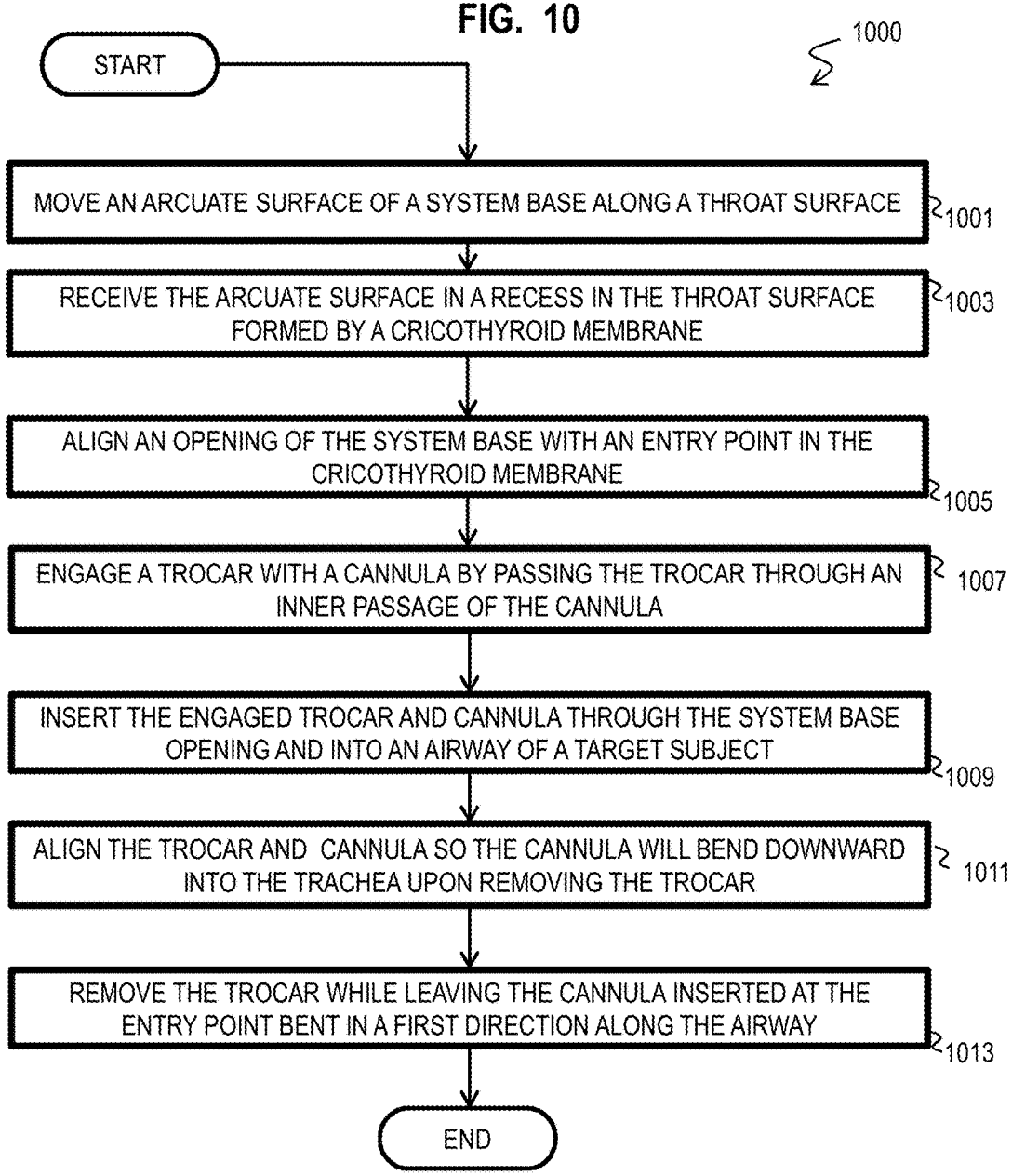

SYSTEM AND METHOD FOR EMERGENCY APNEIC OXYGENATION

CROSS-REFERENCE TO RELATED APPLICATIONS

This application claims benefit of PCT Application No. PCT/US2013/51739 filed Jul. 23, 2013, which in-turn claims the benefit of Provisional Appln. 61/674,414, filed Jul. 23, 2012, under 35 U.S.C. § 119(e). Additionally, this application claims benefit of Provisional Appln. 61/930,043, filed Jan. 22, 2014, under 35 U.S.C. § 119(e).

STATEMENT OF GOVERNMENTAL INTEREST

This work was supported by the U.S. Department of Veterans Affairs, and the Federal Government has certain rights in this invention

BACKGROUND

Apnea refers to suspension of external breathing. During apnea there is little or no movement of the muscles of respiration and the volume of the lungs essentially remains unchanged. Severe tissue damage, brain damage and death can result. Oxygenation during apnea is called apneic oxygenation. Continuous apneic oxygenation delivered to the lower end of the trachea has been found to maintain trauma patients for up to one hour following injury. Despite these findings, there has yet to be an apneic oxygenation catheter developed for use in the field by emergency medical technicians (EMTs) or the military.

A cricothyrotomy is an incision through the cricothyroid membrane above the cricoid cartilage readily evident just above the trachea, and is considered less invasive than an incision through the trachea (tracheotomy) and to have fewer complications. Cricothyrotomy ventilation is often necessary to secure the airway in injuries requiring apneic oxygenation. When there is an obstruction in the airway and endotracheal intubation is not possible, an immediate solution is to insert a tube through a hole in the cricothyroid membrane. In some cases the bypass will allow the patient to breathe on their own. In other instances the bypass will provide an entry way for assisted ventilation and/or drug delivery.

Generally, the devices available to perform emergency cricothyrotomies require a skilled practitioner and require many steps to secure the airway. One example device and procedure are described in U.S. Pat. No. 4,677,978. There, a derivative of the Seldinger method is used making the installation of this device labor intensive. First, a scalpel is used to make an incision into the cricothyroid membrane. Next, an over-the-needle catheter is entered into the airway with a syringe. The syringe and needle are then removed, leaving the catheter in place. Following that, a guide wire is inserted into the catheter, and the catheter is removed. Finally a dilator is inserted over the guide wire and the guide wire is removed.

Other devices such as those described in U.S. Pat. No. 4,869,718 do not use the Seldinger method and therefore require fewer steps. However, these devices only provide a small opening for the catheter and are limited to high frequency jet ventilation.

SUMMARY

Techniques are provided for emergency apneic oxygenation, including devices that provide a more sustainable opening through the cricothyroid membrane.

In a first set of embodiments, a cannula for emergency apneic oxygenation includes a longitudinal inner passage having an inner diameter. A distal portion of the cannula is made of shape memory material shaped to bend in a first direction along the inner passage, and has a first outer diameter greater than the inner diameter. The cannula includes a cannula base having a second outer diameter greater than the first outer diameter. A distance from a distal end of the cannula to a proximal end of the distal portion of the cannula is less than a distance from a surface of a throat of a target subject to a distal surface of an airway of the target subject.

In some of embodiments of the first set, the first outer diameter is less than 10 millimeters.

In a second set of embodiments, a catheter for emergency apneic oxygenation includes a distal portion having a first outer diameter and a first longitudinal inner passage of a first inner diameter less than the first outer diameter. The catheter also includes a proximal portion configured at a proximal end for attachment to a fluid supply and having a second longitudinal inner passage in fluid communication with the first longitudinal inner passage. The catheter still further includes padding at the distal end of the distal portion configured to disperse fluid flow and to prevent damage to a lining of an airway of a target subject.

In some embodiments of the second set, the first outer diameter is less than 10 millimeters.

In some embodiments of the second set, the catheter includes a mark or a collar configured to be placed around the catheter at a particular distance to the proximal side from the distal end of the distal portion. The particular distance is approximately equal to a distance from an entry point into the airway of the target subject to a sub-segmented bronchus of the target subject. In some of these embodiments, the particular distance is in a range from about 5 centimeters to about 15 centimeters.

In a third set of embodiments, a trocar for emergency apneic oxygenation includes a distal portion comprising a tapered cutting edge and a penetration portion disposed proximal to the distal portion and having a diameter less than 10 millimeters. The trocar also includes a stop lip disposed proximal to the penetration portion and having a diameter greater than the diameter of the penetration portion. A distance from a distal end of the stop lip to a distal end of the distal portion is less than about a distance from a surface of a throat of a target subject to a distal surface of an airway of the target subject.

In a fourth set of embodiments, a system for emergency apneic oxygenation includes a cannula and a trocar. The cannula includes an inner passage of an inner diameter, a distal portion and a cannula base. The distal portion has a first outer diameter greater than the inner diameter, and is made of shape memory material shaped to bend in a first direction along the inner passage. The cannula base has a second outer diameter greater than the first outer diameter. The trocar includes a distal portion that includes a cutting edge, a penetration portion and a stop lip. The penetration portion is disposed proximal to the distal portion and has a diameter about equal to the inner diameter. The stop lip is disposed proximal to the penetration portion and has a diameter greater than the diameter of the penetration portion. The trocar is configured to engage the cannula by passing through the inner passage and straightening the bent distal portion of the cannula. When the trocar is engaged, a distance from a distal end of the distal portion of the trocar to a proximal end of the distal portion of the cannula is less than a distance from a surface of a throat of a target subject to a distal surface of an airway of the target subject.

In some embodiments of the fourth set, the system also includes a system base that has a system base opening that has a diameter about equal to the first outer diameter. The system base has an area outside the system base opening that is sufficient to inhibit the cannula base from passing into the airway of the target subject.

In some embodiments of the fourth set, the system also includes a catheter. The catheter is configured to pass through the inner passage of the cannula and be directed by the direction of the bent distal portion of the cannula down the airway of the target subject, after the cannula passes into the airway of the target subject and the trocar is removed.

In a fifth set of embodiments, a kit for emergency apneic oxygenation includes a cannula, a trocar, a base and a catheter. The cannula includes an inner passage of an inner diameter, a distal portion, and a cannula base. The distal portion has a first outer diameter greater than the inner diameter, and is made of shape memory material shaped to bend in a first direction along the inner passage. The cannula base has a second outer diameter greater than the first outer diameter. The trocar is configured to engage the cannula by passing through the inner passage and straightening the bent distal portion of the cannula. The system base has an opening about equal to the first outer diameter and is configured to be placed with the opening centered on an appropriate entry site on a target subject for the trocar engaged with the cannula. The catheter is configured to pass through the cannula after insertion of the cannula into the entry site by the engaged trocar and subsequent removal of the trocar. The catheter has a length that is at least a sum of a first distance from the entry site to a sub-segmented bronchus of the target subject and a second distance from the entry site to a supply of fluid.

In some embodiments of the fifth set, the first outer diameter is less than 10 millimeters.

In a sixth set of embodiments, a method for emergency apneic oxygenation includes cutting an opening of diameter less than 10 millimeters into an airway of a target subject at an entry site. The method also includes passing a distal end of a catheter through the opening and down the airway of the target subject to a sub-segmented bronchus of the target subject. The method further includes connecting a distal end of the catheter to a supply of oxygen and providing oxygen from the supply to the target subject at a rate sufficient to sustain life of the target subject.

In a seventh set of embodiments, a system for emergency apneic oxygenation is provided. The system includes a cannula that has an inner passage of an inner diameter and a distal portion with a first outer diameter. The distal portion is shaped to bend in a first direction along the inner passage. The system also includes a trocar configured to engage the cannula by passing through the inner passage. Additionally, the system includes a system base comprising a panel with an opening of a diameter about equal to the first outer diameter. The system base also includes a bumper with an arcuate surface shaped to be received by a recess formed by a cricothyroid membrane so that the opening is centered on the cricothyroid membrane to provide an entry point for the trocar engaged with the cannula.

In an eighth set of embodiments, a method is provided for emergency apneic oxygenation. The method includes moving an arcuate surface of a system base along a surface of a throat of a target subject. The method also includes receiving the arcuate surface in a recess formed by a cricothyroid membrane along the surface. The method further includes aligning an opening in the system base with an entry point in the cricothyroid membrane based on the receiving step. The method further includes engaging a trocar with a cannula by passing the trocar through an inner passage of the cannula and straightening a bent distal portion of the cannula. The method further includes inserting the engaged trocar and cannula through the opening in the system base and the entry point in the cricothyroid membrane and into an airway of the target subject.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIG. 2A through FIG. 2D are block diagrams that illustrate example use of the components of FIG. 1A through FIG. 1D, according to an embodiment;

FIG. 5A through FIG. 5H are block diagrams that illustrate example variations in catheters from that depicted in FIG. 1D, according to various embodiments;

FIG. 9 is a block diagram that illustrates an example use of the components of FIG. 1A, FIG. 1B, FIG. 1D and FIG. 7A through FIG. 7D, according to an embodiment; and FIG. 10 is a flow diagram that illustrates an example of a method for providing emergency apneic oxygenation, according to an embodiment.

DETAILED DESCRIPTION

Figure 1A:
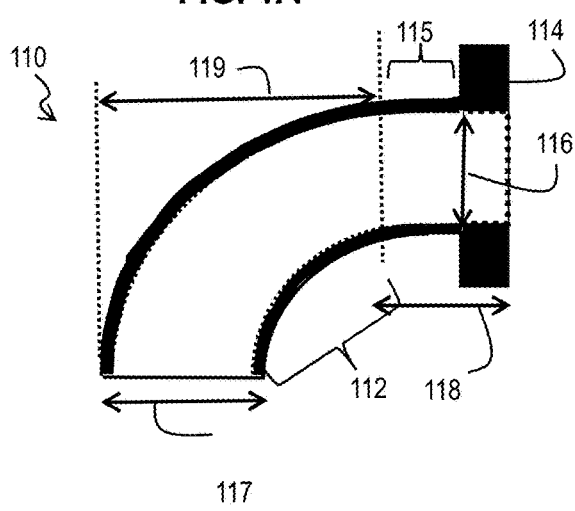
FIG. 1A through FIG. 1D are block diagrams that illustrate example components of a apnea oxygenation kit, according to an embodiment.

A method, apparatus, system and kit are described for emergency apneic oxygenation. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Some embodiments of the invention are described below in the context of an emergency, such as a trauma caused by natural disasters, accidents, or acts of war or tenor, suffered by an adult. However, the invention is not limited to this context. In other embodiments the procedure or device is employed on children and in clinical or hospital settings, such as in first aid, preparation for or recovery from surgery, or response to power failures in the operating room, or wherever cardiopulmonary resuscitation (CPR) or automated defibrillator is employed, such as for response to heart attack, pulmonary embolism, significant overwhelming infection, and choking.

As used herein, a "proximal" end or face shall be construed as the end or face that is closest to the user when the device is in use. As defined herein, a "distal" end or face shall be understood as the end or face that is closest to, or deepest inside, the patient, and farthest from the user, when the device is in use. As used herein, diameter refers to a shortest distance through an object, whether the object has a circular cross section or not. As used herein, a subject is a person or animal, and a target subject is a subject that is to receive apneic oxygenation. In some embodiments, the target subject is an individual person; in some embodiments, the target subject is a population of individuals, such as adults or sub-teenaged children. In such embodiments, the values of characteristics (such as values of airway diameter and length) of the target subject are an average or range of characteristics of the population. As used herein, a fluid means any material that flows at ambient temperatures, including liquids (e.g., medications) and gases (e.g., oxygen gas).

Although processes, equipment, and data structures are depicted in FIG. 1 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

FIG. 1A through FIG. 1D are block diagrams that illustrate example components of an apnea oxygenation kit, according to an embodiment. In the illustrated embodiment, the components of the kit are shown with circular cross sections; however, in other embodiments other cross sections are used, such as oval cross sections, polygonal cross sections, lens shaped cross sections, and rectilinear cross sections.

FIG. 1A is a block diagram that illustrates an example cross section through a cannula 110 with an inner passage of inner diameter 116 configured for passing one or more catheters. The cannula 110 is configured to be inserted through a wall at the front of the target subject's airway, e.g., above the cricoid cartilage, and into the target subject's airway. Thus it extends from the skin surface of a throat of a target subject into the airway.

A distal portion 112 of the cannula is made of a shape memory material and is bent in a first direction (downward in the illustrated view) as one progresses through the inner passage from a proximal end to a distal end. The distal portion 112 has an outer diameter 117, larger than the inner diameter 116. At the proximal end of cannula 110 is a cannula base 114, with an outer diameter greater than the outer diameter 117 of the distal portion 112 of the cannula. In some embodiments, there is a straight portion 115 of the cannula between the bent distal portion 112 and the cannula base portion 114. Suitable shape memory materials are known in the art, for example, titanium, thin stainless steel, and nickel titanium alloy (also called Nitinol). When in place in the wall of a target subject's airway, the downward bend of the distal portion 112 of the cannula directs a catheter threaded through the cannula downward in the subject's airways toward the lungs. This downward bias provides a very advantageous control when an operator is working in unguided and difficult conditions, such as darkness. The larger outer diameter of the cannula base 114 prevents the cannula 110 from falling through a hole with a diameter closely matching the outer diameter 117 of the distal portion 112 of the cannula, while allowing the entire distal portion 112, and in some embodiments, a straight portion 115 to pass into the hole. The cannula base 114 has thickness 118 and is made of any suitable rigid or semi-rigid material including the same materials as the distal portion or separate materials such as stainless steel, titanium, nitinol, plastics or other types of polymers, or some combination.

It is also desirable that the bend in the cannula take place within the airway of the target subject without contacting or penetrating the back wall of the airway. Thus, it is advantageous for a distance 119 from a distal end of the cannula to a proximal end of the distal portion 112 of the cannula to be less than a distance from a surface of a throat of a target subject to a distal surface of an airway of the target subject. In some embodiments, the length of the distal portion 112 is so constrained. In some embodiments in which the distal face of the cannula base 114 is flush with the skin of the target subject, the distance from the distal face of cannula base 114 to the distal end of the cannula is advantageously less than the distance from a surface of a throat of a target subject to a distal surface of an airway of the target subject to avoid damaging or perforating the back wall of the airway.

Currently, apneic oxygenation uses holes into the airway which are a centimeter (10 millimeters) or more. Preferably, smaller incisions are made to reduce blood loss and chances for complications such as infection. By passing catheters attached to an oxygen supply, a smaller opening can be used. Thus, in various embodiments, the outer diameter 117 of the distal portion of the cannula is less than 10 millimeters and preferably in a range from about 3 millimeters to about 4 millimeters. The inner diameter 116 is sufficient to pass at least one catheter to supply oxygen and is preferably in a range from about 2 millimeters to about 3 millimeters. Larger inner diameters are used for bigger catheters or for multiple catheters, in various embodiments.

Figure 1B:
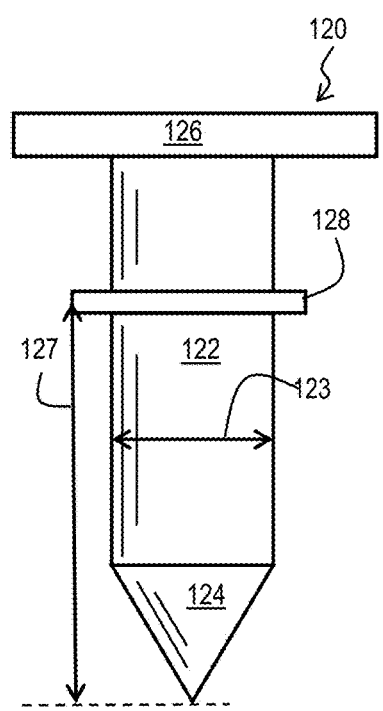

FIG. 1B is a block diagram that illustrates an example trocar 120, according to an embodiment. Trocar 120 (also called an obturator) is used to cut a hole from the skin of the throat into the airway of the target subject without damaging the back wall of the airway of the target subject. The trocar is made of any suitable rigid material, such as stainless steel, carbon steel, titanium, cobalt chrome, plastics or other types of polymers, or some combination. The trocar 120 is further configured to leave the cannula in place in the hole so cut. In the illustrated embodiment, the trocar includes a tapered piercing tip 124 at a distal end and a penetration portion 122 disposed proximal to the distal portion 124 and having a diameter 123 about equal to an inner diameter 116 of the cannula 110. Thus the diameter 123 is less than about 10 millimeters and preferably less than 4 millimeters, and most preferably for use with a single catheter in a range from about 2 millimeters to about 3 millimeters. The piercing tip 124 is generally conical in shape. However, in some embodiments the piercing tip has more than one cutting edge. The trocar 120 also includes a stop lip 128 disposed proximal to the penetration portion and having a diameter greater than the diameter of the penetration portion. The stop lip 128 is configured to keep a cannula 110 from sliding along the trocar during insertion. In some embodiments, proximal to the stop lip is a handle 126 that is more easily grasped by an operator.

To keep from damaging a back wall of the airway of the target subject, a distance 127 from a distal end of the stop lip 128 to a distal end of the distal portion is less than a distance from a surface of a throat of a target subject to a distal surface of an airway of the target subject. In some embodiments, in which the cannula 110 with base of thickness 118 is disposed distal to the stop lip, a distance 127 minus thickness 118 is constrained to be less than the distance from the skin of the throat to the back wall of the airway. In some embodiments, in which the cannula 110 with base of thickness 118 and system base of thickness 134 is disposed distal to the stop lip and cannula base 114, a distance 127 minus thickness 118 and minus thickness 134 is constrained to be less than the distance from the skin of the throat to the back wall of the airway. In various embodiments, depending on the target patient, the distance 127 is selected in a range from about 5 millimeters to about 35 millimeters, and preferably about 25 millimeters. The trocar 120 is configured to engage the cannula 110 by passing the piercing tip 124 of the trocar through the inner passage of the cannula base 114 and thence into the inner passage of the bent distal portion 112, and straightening the bent distal portion 112 of the cannula.

Figure 1C:
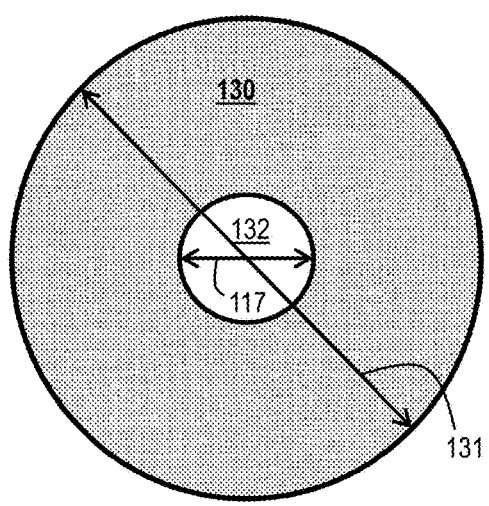

FIG. 1C is a block diagram that illustrates an example system base 130, according to an embodiment. System base 130 has diameter 131 and includes a system base opening 132 of diameter about equal to the outer diameter 117 of cannula 110. As shown in FIG. 2A, system base also has thickness 134. The system base 130 has an area outside the system base opening 132 that is sufficient to inhibit the cannula base 114 from passing into the airway of the target subject. The system base 130 also provides an advantage of locating the entry point incision on the throat of the target subject as a center of the opening 132. The system base 130 is made of any suitable rigid or semi-rigid material, including molded plastic, other types of polymers, stainless steel, titanium, or cobalt chrome, or some combination. In various embodiments, the system base has a diameter in a range from about 5 millimeters to about 15 millimeters. Although appearing circular in FIG. 1C, in various other embodiments, the system base 130 has a different shape, such as a rectangle or shape to match the contours of the neck of the target subject.

Figure 1D:
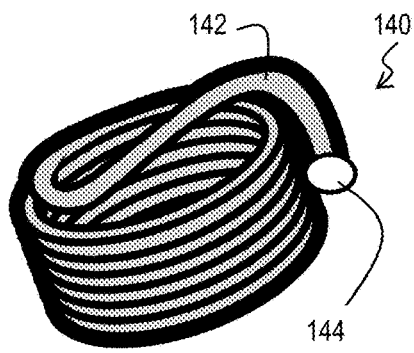

FIG. 1D is a block diagram that illustrates an example catheter 140, according to an embodiment. Catheter 140 is a long tube 142 of flexible non-toxic and sterile material, such as silicon plastic or other types of polymers with a fitting 144 for attachment to fluid supply, such as an oxygen supply or a medicine supply. A tube with outer diameter of 2 to 3 millimeters was found suitable for delivering sufficient oxygen to a target subject without exposing the subject to the risks associated with a larger opening, including excessive bleeding, infection and loss of life. The inner diameter is selected in a range from about 1 millimeter to about 2 millimeters. A distal portion is configured to be inserted into an airway of the subject patient and a distal end open to allow free fluid flow, for example into a sub-segmented bronchus of the target subject. A proximal end is configured for attachment to a fluid supply such as an oxygen supply or medicine supply. A proximal portion connects an entry point into the airway of the target subject to the proximal end and also comprises a second inner and outer diameter that are the same as in the distal portion in some embodiments, and different in other embodiments. The second longitudinal inner passage is in fluid communication with the first longitudinal inner passage.

In other embodiments, the kit includes additional or fewer components. For example, in some embodiments, the cannula base 114 has an outer diameter sufficient to prevent falling into any opening for the distal portion 112, and the system base is omitted. In various other embodiments, other components are added, such as those described in more detail below.

Figure 2C:
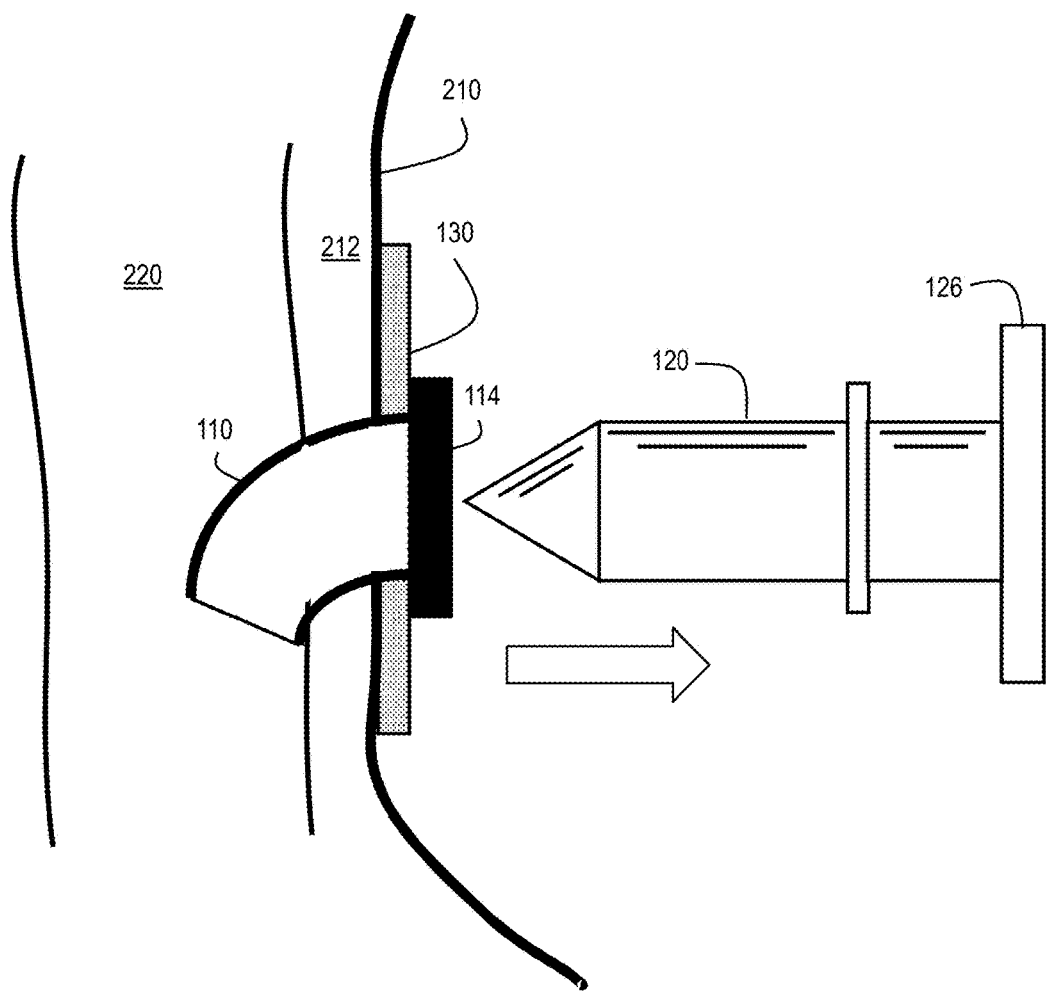

FIG. 2A through FIG. 2D are block diagrams that illustrate example use of the components of FIG. 1A through FIG. 1D, according to an embodiment. As shown in FIG. 2A, a cross section of the throat of a target subject is illustrated by skin 210, front wall 212 of airway, and airway 220 having width 222. The system base 130 of thickness 134 is laid on the skin 210 of the subject to expose in the opening 132 an entry point 230 for the incision. A distance 224 extends from the distal face of the system base 130 to the back wall of the airway; and a distance 223 extends from the proximal face of the system base 130 to the back wall of the airway.

The trocar 120 has engaged the cannula 110 and straightened the bent distal portion. The proximal face of the cannula base 114 is flush with the distal face of the stop lip 128. The incision is made by driving the trocar engaged with the cannula in the direction of the open arrow.

As shown in FIG. 2B, the trocar 120 cuts through the skin 210 and front wall 212 of the target subject airway 220 with the cannula 110 in place. The back wall of the airway is not disturbed so long as the distance 127 from the distal end of trocar to the stop lip minus the thickness 118 of the cannula base minus the thickness 134 of the system base is less than the distance from the skin 210 to the back wall of the airway 220. In some embodiments, markings on cannula base 114 indicate the direction of bending of the cannula with the trocar disengaged. This mark is oriented so that the cannula 110 will bend downward when the trocar is removed.

As shown in FIG. 2C, the trocar 120 is removed from the entry site by pulling on the handle 126 in the direction of the open arrow. In some embodiments, the base 114 of cannula is held in place while the trocar 120 is removed. The system base 130 prevents the base 114 of cannula 110 from entering the hole made by the piercing tip 124 of the trocar 120. With the trocar disengaged, the distal portion of cannula 110 assumes its original shape, and points downward in the airway towards the lungs of the target subject, as desired.

Figure 2D:
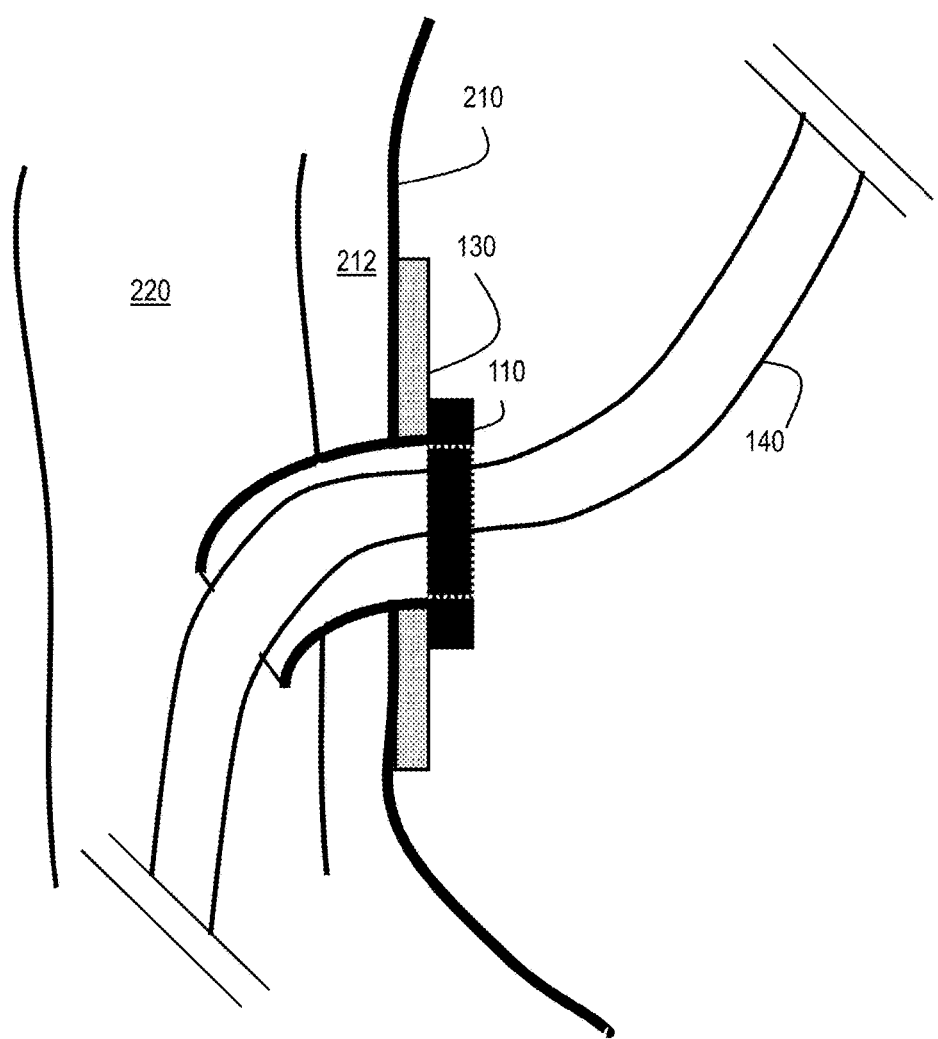

As shown in FIG. 2D, a catheter 140 is inserted through the inner passage of the cannula 110 and is automatically directed downward inside the airway toward the lung because the cannula has remembered its downward bent shape.

Figure 3A:
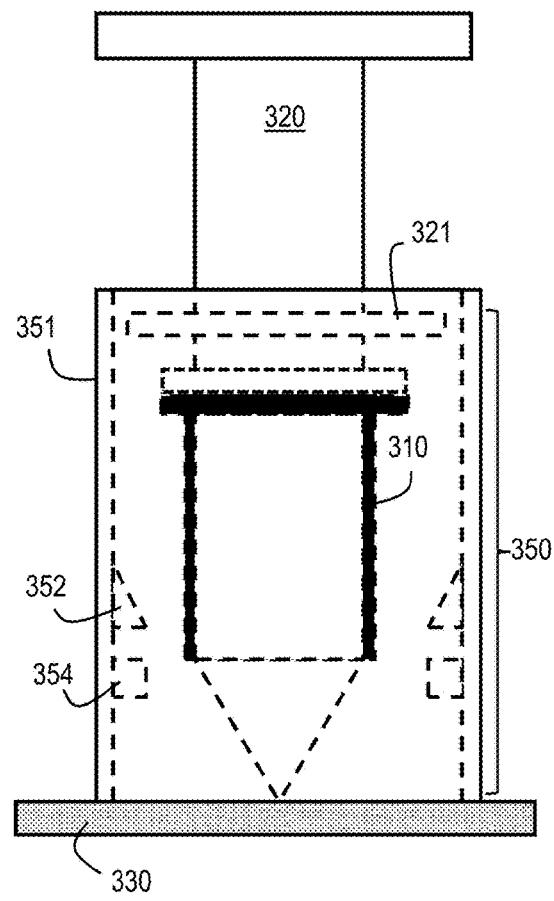
FIG. 3A through FIG. 3E are block diagrams that illustrate example variations to the kit of FIG. 1A through FIG. 1D, including a protective casing according to various embodiments.
Figure 3B:
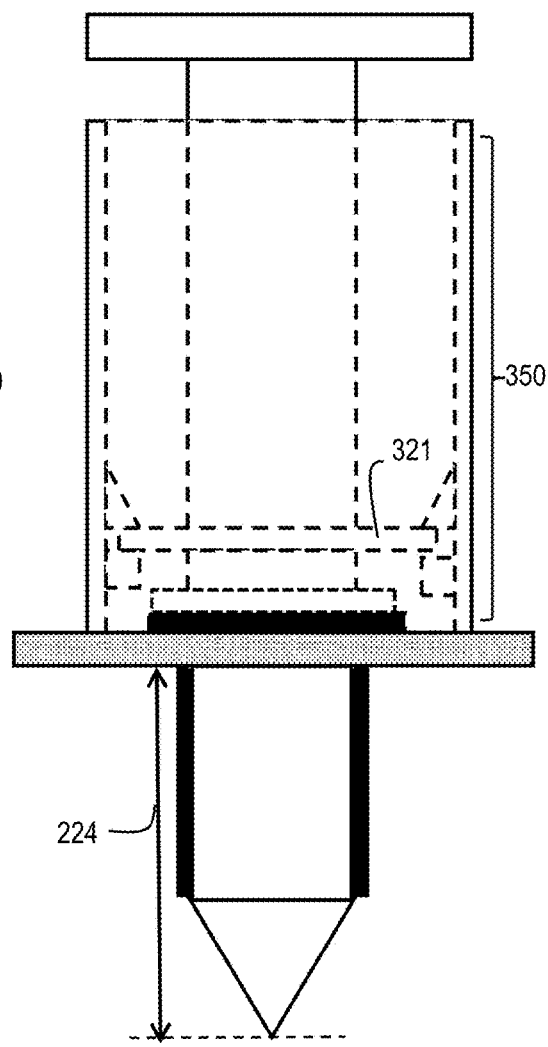

FIG. 3A through FIG. 3E and FIG. 4 are block diagrams that illustrate example variations to the kit of FIG. 1A through FIG. 1D, including a protective casing, according to various embodiments. In some embodiments the device further comprises a protective casing 350. Once the body cavity is penetrated, as shown in FIG. 3B, the trocar 320 and optional protective casing 350 may be removed. The cannula 310 and base 330 remain in place. In these embodiments, the trocar includes a locking disk 321 that has a diameter larger than stop lip 328. The diameter and length depend on dimensions of any securing mechanism 352 and 354 on the protective casing. The preferred dimensions fix locking disk 321 into the securing mechanism 352 and 354 when in place.

Figure 3C:
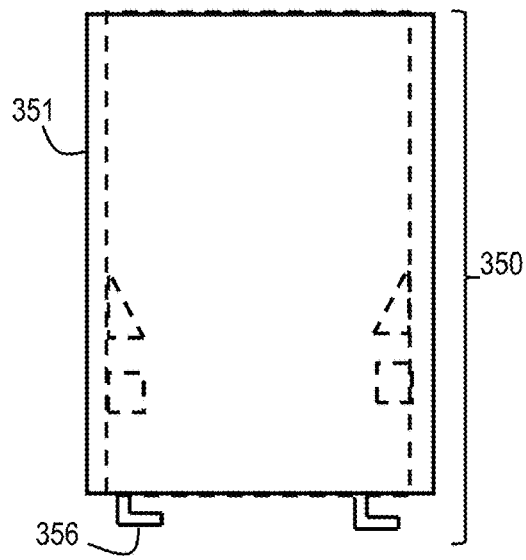

Referring to FIG. 3C, the protective casing 350 comprises an outer casing 351, a securing mechanism 352, 354 for the locking ring of the trocar 320, and one or more fasteners 356. Outer casing 351 is made of a generally rigid material, such as metal, plastics or other types of polymers, and has an outer diameter of between about 0.5 centimeters to about 4 centimeters. The interior diameter of outer casing 351 is between about 0.49 centimeters and about 3.99 centimeters. The length of outer casing 351 is between about 0.5 centimeters to about 4 centimeters. Securing mechanism 352 and 354 is located somewhere along the interior surface of the outer casing 351. Securing mechanism 352 and 354 may cover the entire circumference of the outer casing 351 or there may be one or more parts spaced around the circumference of the outer casing 351. The purpose of the securing mechanism is to fix the locking ring of the trocar in place when the trocar tip is inserted into the subject. The securing mechanism also serves as a safety mechanism to prevent the user from pressing the trocar too far into the subject.

In some embodiments the securing mechanism 352 and 354 is located at different locations on the outer casing interior surface to conform to different patient sizes. In other embodiments, the locking ring is fixed by the securing mechanism 352 and 354 before the snaps of the cannula are fixed to the base. For these embodiments, the cannula is preferably manually fixed after the trocar and protective casing are removed. It is contemplated that this embodiment will provide for a longer cannula without risking unwanted damage by the trocar.

Referring to FIG. 3C, one or more fasteners 356 are located at the base of the protective casing. The fasteners 356 are used to secure the protective casing 350 to the base 330 as depicted in FIG. 3A and FIG. 3B. In one embodiment, the protective casing 350 is removed from the base by rotating the protective casing 350. In this example the rotation frees the one or more fasteners 356 from the base. Other types of fasteners may be used instead. For example, the fasteners 356 may snap into the base.

Figure 3D:
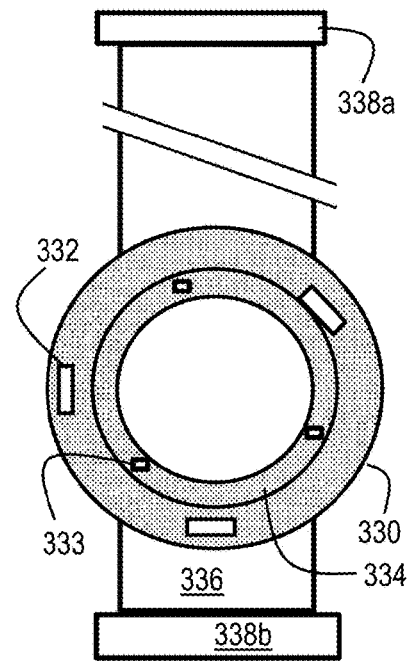
Figure 3E:
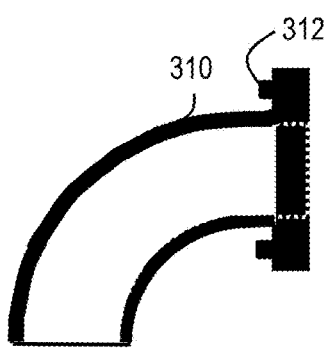

FIG. 3D depicts a proximal face of the system base 330. The base 330 comprises a generally disk shaped surface. Base 330 further comprises one or more notches 332 for the fasteners of the outer casing. The shape of the notches 332 depends on the configuration of the protective casing fasteners. In one example embodiment the notches 332 are L-shaped to allow for the release of the protective casing when the protective casing is rotated. In some embodiments, the base 330 also comprises one or more notches 333 which receive one or more snaps 312 of the cannula 310 as depicted in FIG. 3E. The specific configuration of notches 332 and 333 may vary in other embodiments. In consideration of the teaching provided herein, one having ordinary skill in the art would recognize other configurations that while not specifically identified, are still within the overall spirit and scope of this invention.

Referring again to FIG. 3D, in some embodiments the system base 330 is attached to a strap 336 that wraps around the neck of the target subject, and is held in place by complementary buckle 338a and clasp 338b. In some embodiments, strap 336 is attached to system base 330 by eyelets that form part of base 330. In the illustrated embodiment, the system base 330 includes an inner annulus 334 that is slightly recessed for accepting the distal face of cannula base 114.

Figure 4:
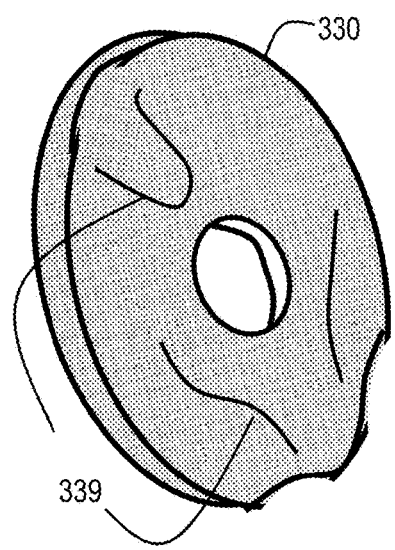
FIG. 4 is a block diagram that illustrates an example distal face of the system base 330, according to some embodiments.

FIG. 4 depicts a distal face of the system base 330, according to some embodiments. In the illustrated embodiment, the distal face is contoured with one or more contours 339 so that the system base 330 settles most securely when the opening of the system base is properly positioned over a preferred entry point. Thus, a system base is configured with a shape that follows contours of a throat of the target subject so that the system opening is centered on a location appropriate as an entry point for a catheter for emergency apneic oxygenation.

Figure 5B:
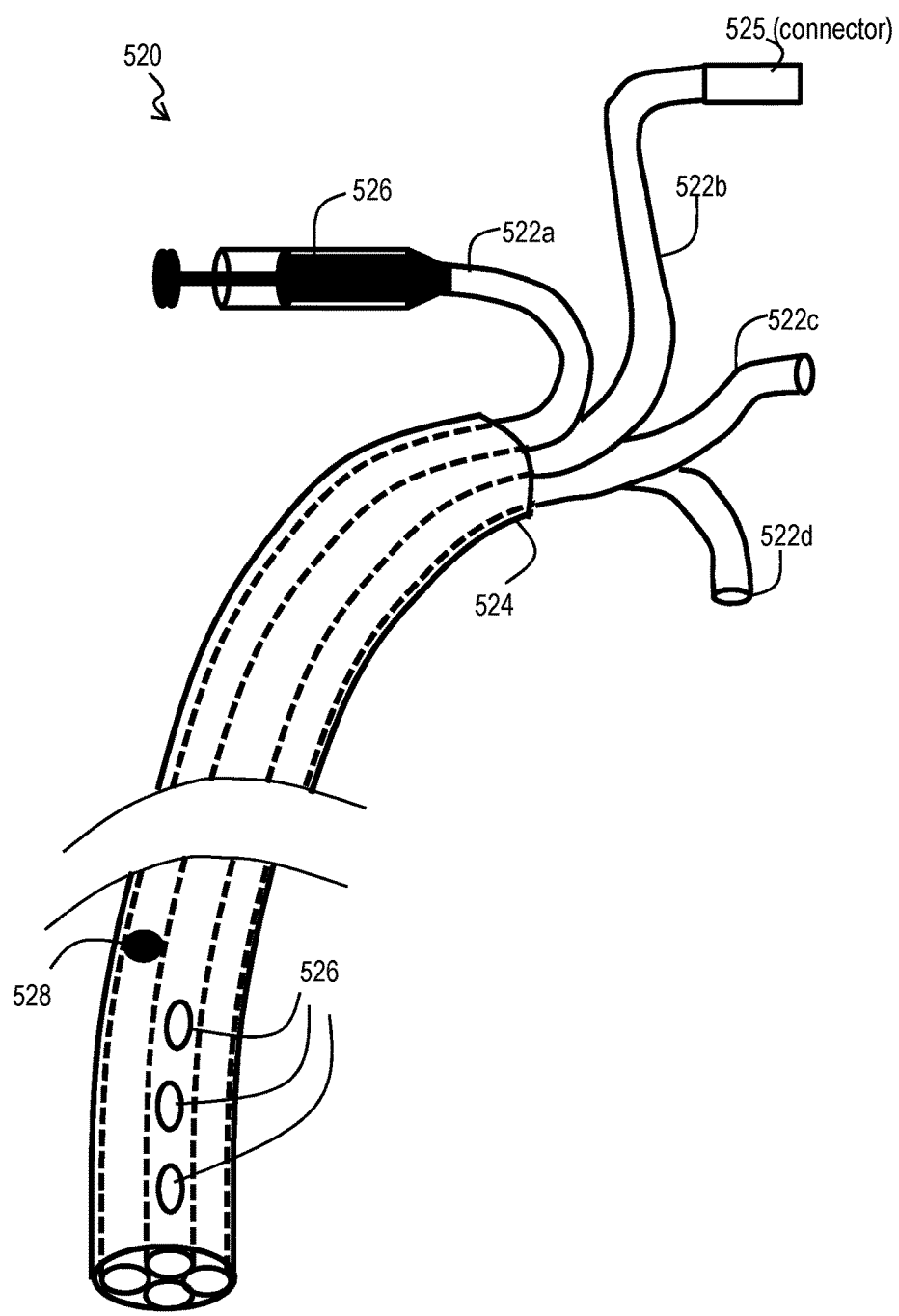

FIG. 5A through FIG. 5H are block diagrams that illustrate example variations in catheters from that depicted in FIG. 1D, according to various embodiments. FIG. 5A is a block diagram that illustrates an apneic oxygenation catheter 500 according to an embodiment. Catheter 500 comprises an elongated shaft 501, having a proximal end 519 and a distal end 509. Catheter 500 further comprises one or more ventilation ports called apertures 506 at the distal portion of the shaft and a connection element 514 at the proximal end. The connection element 514 is depicted connected to a fluid supply tank 518, such as an oxygen supply tank. Apertures 506 may be located in any pattern desirable. For example, in some embodiments a plurality of apertures are located within a particular distance of the distal end of the distal portion, where each aperture is configured to permit fluid flow between the first longitudinal inner passage and an outside of the catheter. In some of these embodiments, the particular distance is less than a distance from a sub-segmented bronchus of the target subject to a mainstem bronchus of the target subject.

In some embodiments, the catheter 500 includes a collar 516 to mark the particular distance 507 of the catheter to be inserted through the cannula and into the airway of the target subject. The collar is configured to be placed around the catheter at a particular distance 507 to the proximal side from the distal end of the distal portion, wherein the particular distance 507 is approximately equal to a distance from an entry point into the airway of the target subject to a sub-segmented bronchus of the target subject. In some embodiments, the particular distance is in a range from about 5 centimeters to about 15 centimeters. In some embodiments, the collar is moveable along that range. In some embodiments, gradation marks are included along the shaft in addition to or instead of the collar 516. An advantage of the collar 516 is that the collar presents a physical stop when it encounters the cannula. This physical stop allows an operator to detect, without having to look at the catheter, when sufficient length has been inserted into the airway. In some embodiments, the inner and outer diameter of the catheter have one set of values on a distal portion 502 to the distal side of the collar 516, and another set of values on a proximal portion 512 to the proximal side of the collar 516.

Oxygenation catheter 500 advantageously includes padding 504 at the distal end. Padding 504 in various embodiments includes, for example, a balloon, a sponge, or other attachment that would help prevent injury to the trachea or bronchi during insertion or dispense air in 360 degrees or both, in some combination. In some embodiments, a dissolvable capsule at the distal end is used to reduce the risk of injury when the device is inserted, alone or in combination with the padding.

Catheter 500 may further comprise one or more balloons 508 along the shaft 502. The purpose of balloon 508 is to secure the device in the patient, in some embodiments; or to concentrate the oxygen to a certain area of the lungs, in some embodiments. The one or more balloons 508 may be located at various locations along the length of shaft 502 depending on the particular needs. Balloon 508 may be inflated using the oxygen source or it may have a separate lumen in which a separate inflation device is attached.

The apneic oxygenation catheter may have more than one lumen. FIG. 5B depicts a quadruple lumen embodiment 520 having a drug delivery lumen 522a and an oxygen delivery lumen 522b inside catheter sheath 524 with apertures 526 into the lumen 522b. In other embodiments, the catheter may have one, two, three or more lumens. The proximal end of drug delivery lumen 522a is configured to be readily attached to containers 526 of drugs. Catheter 520 in some embodiments further comprises a fenestrated diaphragm 528 inside drug delivery lumen 522a. Diaphragm 528 enables small drug particle dispersion for better lung absorption. Example drugs that may be used include, but are not limited to, epinephrine, atropine, and lidocaine. Thus, each of the first longitudinal inner passage in a distal portion and the second longitudinal inner passage in a proximal portion is divided into a plurality of lumens, each lumen in the first longitudinal passage in fluid communication with a corresponding lumen in the second longitudinal passage.

The oxygenation catheter may also have a bifurcated or trifurcated distal end, below a catheter sheath, to provide for additional oxygenation. FIG. 5C is a block diagram that illustrates an example trifurcated catheter 530 with three lumens 532a, 532b and 532c, each configured with connectors 535a, 535b, 535c, respectively, for connecting to a fluid supply tanks, such as an oxygen tank. FIG. 5F is a block diagram that illustrates an example trifurcated catheter 544 deployed in a lung 590. The branch may be located at the base of the trachea or further down in the lung 590. FIG. 5F depicts trachea 592 and a branch in one mainstem bronchus, with each different lumen 542a, 542b, 542c, located in a different sub-segmented bronchus of bronchi 593a, 593b, 593c, respectively.

Figure 5D:
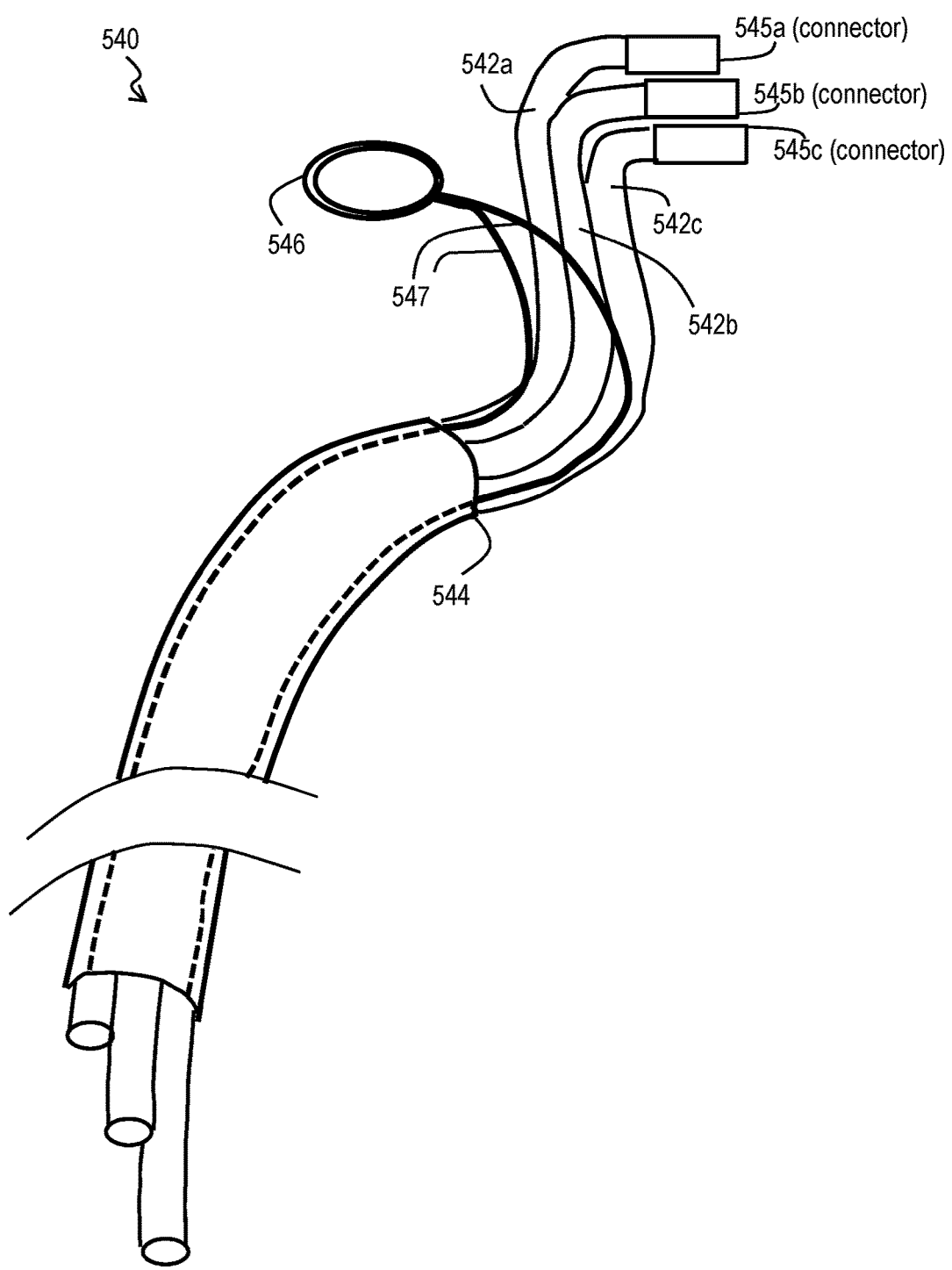
Figure 5E:
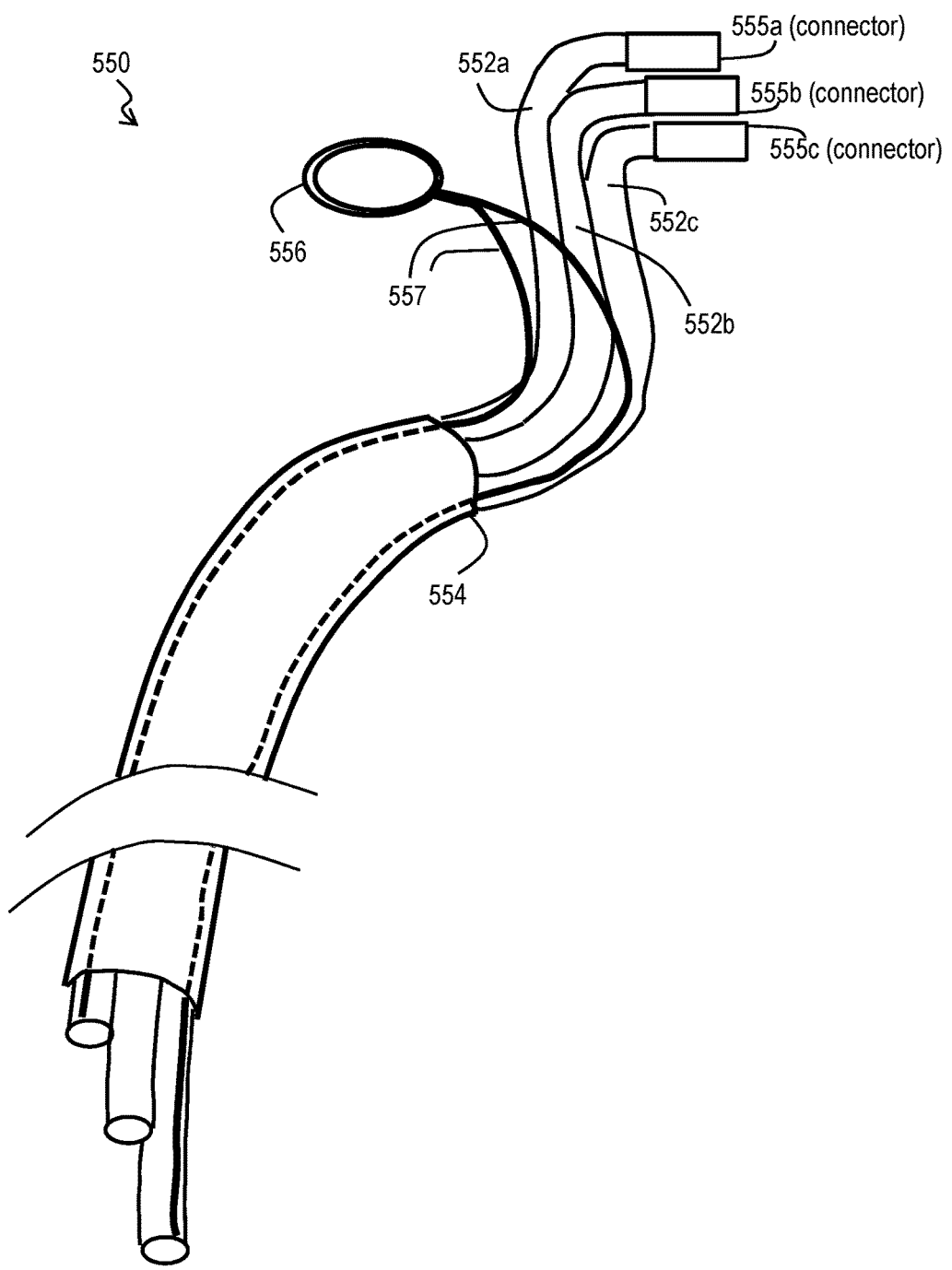
Figure 5F:
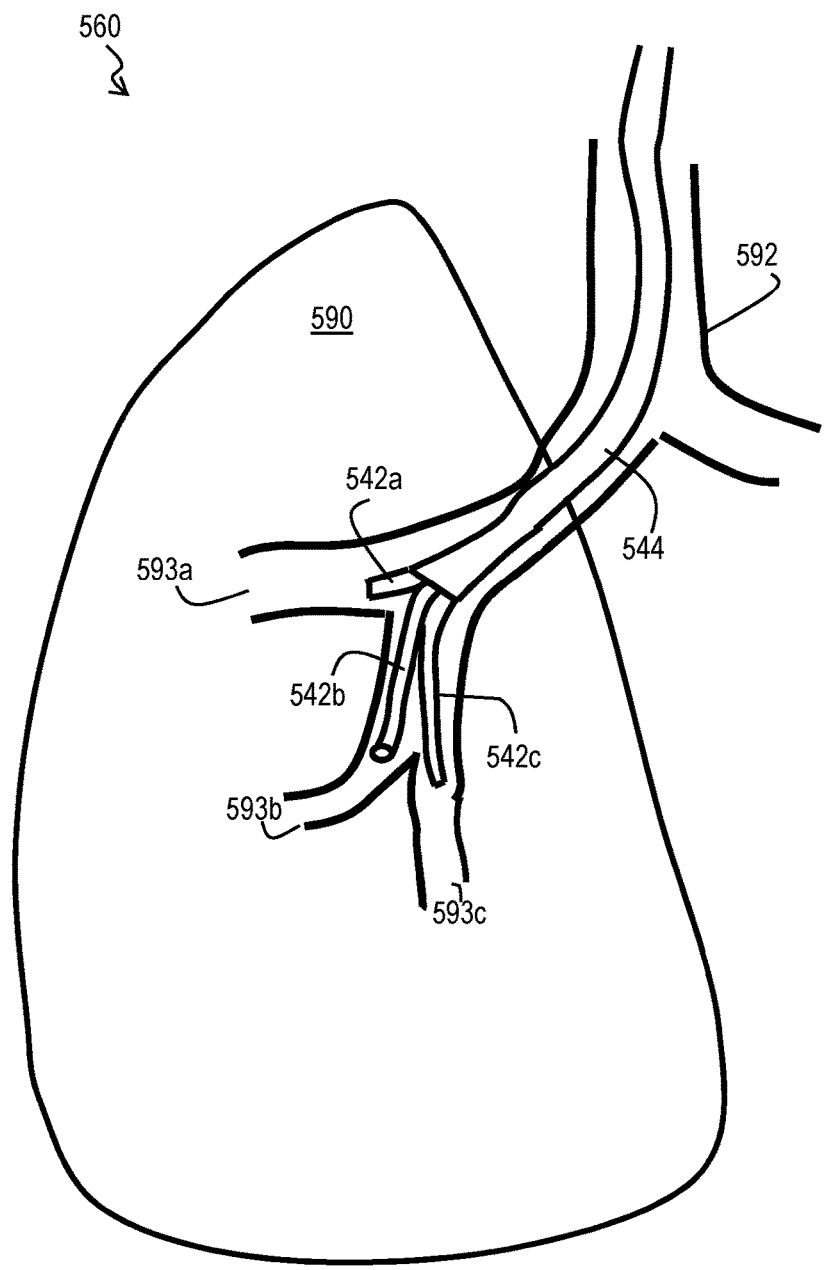

Referring now to FIG. 5D and FIG. 5F, one possible deployment method for the trifurcated system is a pull string. In FIG. 5D separate lumen 542a, 542b, 542c with connectors 545a, 545b, 545c, respectively, are controlled at the distal end by pull string ring 546 connected to pull strings 547. When pulled, the strings 547 retract a sheath 544 of the catheter, exposing each lumen in succession. By feel, the operator may leave one lumen near each of different sub-segmented bronchi. In FIG. 5E, separate lumen 552a, 552b, 552c with connectors 555a, 555b, 555c, respectively, within sheath 554, are controlled at the distal end by pull string ring 556 connected to pull strings 557. When pulled, the strings 557 retract each lumen in succession. Here, each of one or more distal ends (branches) is connected to a pull string 557 to coordinate the deployment of each distal end of lumen 552a, 552b, 552c.

Figure 5G:
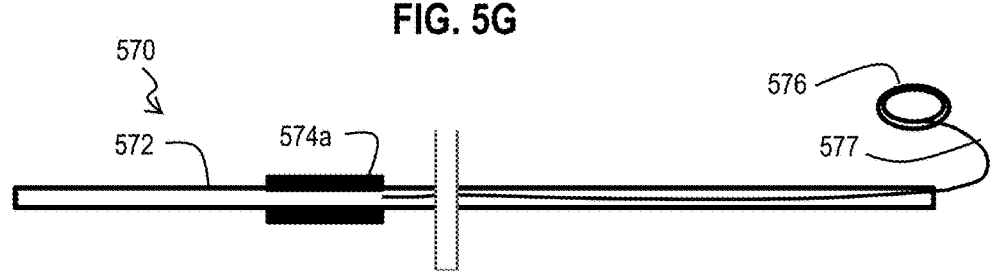
Figure 5H:
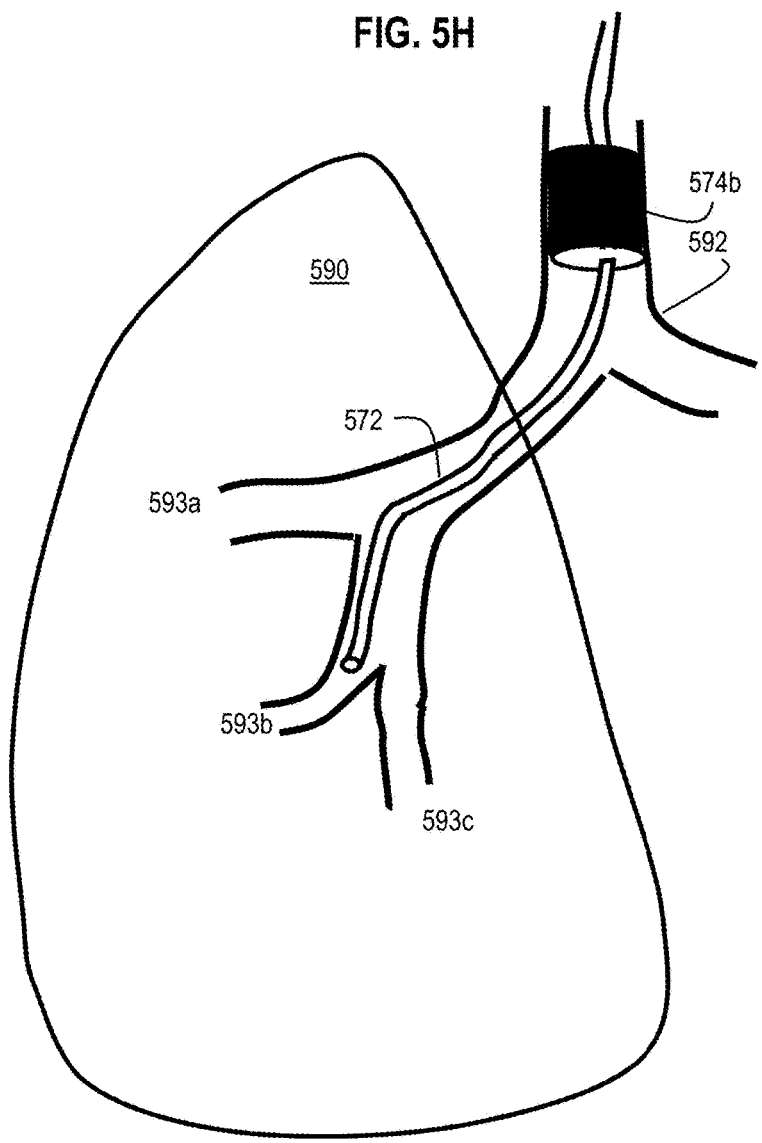

FIG. 5G is a block diagram that illustrates an example alternative securing mechanism to the balloon 508 of FIG. 5A. Catheter 570 includes a shaft 572 and expandable device 574a connected by guide wire 577 to ring 576. When ring 576 is pulled, expandable device 574a expands. Expandable device 574a is used to anchor the catheter 570 in the airway of the target subject, as depicted in FIG. 5H. FIG. 5H is a block diagram that illustrates an example location of catheter shaft 572 and expanding device 574b in an expanded configuration in a lung 590 of a target subject. The distal end of shaft 572 is located in sub-segmented bronchus 593b of sub-segmented bronchi 593a, 593b, 593c. In an example embodiment, expandable device 574a is made of nitinol. However, other biocompatible materials, such as metals, plastics or other polymers, or some combination, are used in other embodiments. In some embodiments, expandable device 574a is a silicon balloon or similar type feature is used. Catheter 570 further comprises a guide wire channel in some embodiments.

Thus various embodiments include an anchoring device disposed outside the catheter at a particular distance proximal to the distal end of the distal portion of the catheter, wherein the anchoring device is configured to assume a first shape of small cross sectional area and a second shape of larger cross sectional area sufficient to fill the airway of the target subject outside the catheter.

Various combinations of the devices described above may be combined into a kit for emergency use. In addition to the oxygenation catheter and a cannula-trocar crycothyrotomy intubation assembly, a kit may further comprise an oxygen source. It is contemplated that an oxygen tank capable of containing enough oxygen to maintain an average sized patient for at least an hour would be preferable. However, larger or smaller tanks may be used in the kit. A person having ordinary skill in the art would be capable of determining the most appropriate tank size. In some example embodiments, vials of drugs such as, for instance, epinephrine, atropine, or lidocaine are provided with the kit.

A method is described for providing apneic oxygenation, according to some embodiments. Although steps are described as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. A method for emergency apneic oxygenation includes cutting an opening of diameter less than 10 millimeters into an airway of a target subject at an entry site. The method also includes passing a distal end of a catheter through the opening and down the airway of the target subject to a sub-segmented bronchus of the target subject. The method still further includes connecting a distal end of the catheter to a supply of oxygen, and providing oxygen from the supply to the target subject at a rate sufficient to sustain life of the target subject.

In some embodiments, cutting the opening further comprises inserting at the entry site a trocar engaged with a cannula comprising a distal end of shape memory material, wherein the cannula without trocar engaged is bent in a first direction. The trocar is inserted so that the first direction is directed downward in the airway of the target subject. The step further includes removing the trocar while leaving the cannula inserted at the entry site.

In some embodiments, inserting the trocar engaged with the cannula at the entry site further includes placing a system base on a throat of the target subject so that an opening of the system base is centered on the entry site, and inserting the trocar engaged with the cannula through the opening in the system base.

In some embodiments, passing the distal end of the catheter through the opening further comprises passing the distal end of the catheter through the cannula.

In some embodiments, the opening into the airway of the target subject is in a range from about 2 millimeters to about 3 millimeters.

Figure 6A:
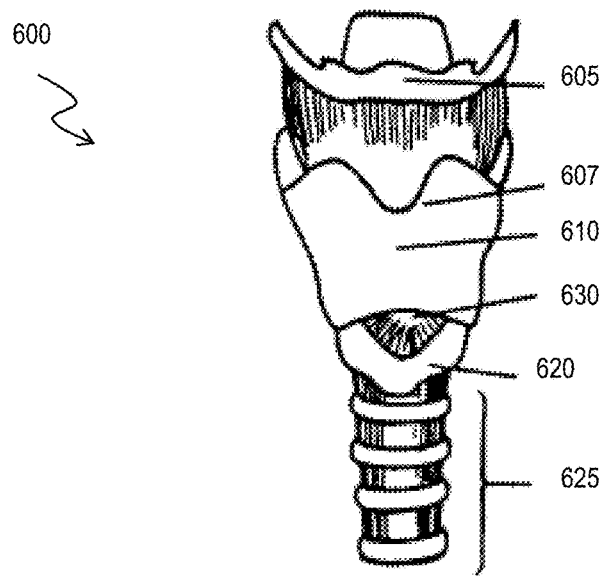
FIG. 6A and FIG. 6B are respective front and side views of a cricothyroid membrane in a target subject.
Figure 6B:
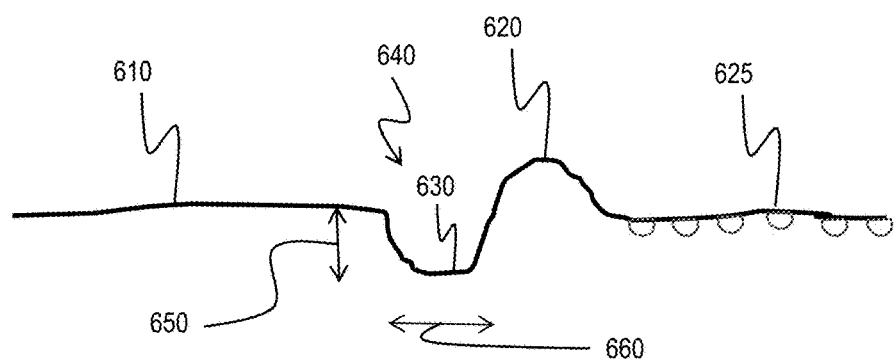

FIG. 6A and FIG. 6B are respective front and side views of a cricothyroid membrane 630 along a throat surface of a target subject 600, according to an embodiment. The cricothyroid membrane 630 is positioned above the trachea 625 and the cricoid cartilage 620 and below the thyroid cartilage 610. As depicted in FIG. 6B, a recess 640 is formed by the cricothyroid membrane 630 between the thyroid cartilage 610 and the cricoid cartilage 620. In one embodiment, the recess 630 has a depth 650 within a range of 8-12 millimeters, such as 10.4 millimeters, for example. In another embodiment, the recess 630 has a length 660 within a range of 7-9 millimeters, such as 8.2 millimeters, for example, along the surface of the throat. As appreciated by one skilled in the art, the cricothyroid membrane 630 is a relatively soft pliable tissue, relative to the more rigid tissue that forms the thyroid cartilage 610 and the cricoid cartilage 620. The cricothyroid membrane 630 is located below the Adam's apple 607 in a male target subject and is also located below the hyoid cartilage 605.

FIG. 7A through FIG. 7D are block diagrams that illustrate a variation in the system base from that depicted in FIG. 1C, according to an embodiment. The system base 700 includes a panel 702 with a system base opening 706 that has a diameter 708 about equal to the first outer diameter of the cannula and in a range of about 0.25 to about 2.5 centimeters. In an embodiment, the panel 702 is a disc-shaped panel with a length or diameter 720 in a range of about 5 to about 20 millimeters and a thickness 717 in a range of about 0.7 to about 2 millimeters. Although the embodiment of FIGS. 7A through 7D depict that the panel 702 as a disc-shaped panel, the panel may take any shape that is capable of facilitating the emergency apneic oxygenation procedure discussed herein.

The system base 700 also includes a bumper 704 with an arcuate surface 710 that is shaped to be received by the recess 640 formed by the cricothyroid membrane 630 between the thyroid cartilage 610 and the cricoid cartilage 620 of the target subject 600. When the arcuate surface 710 of the bumper 704 is received by the recess 640, the system base opening 706 is centered on the cricothyroid membrane 630 to provide an entry point for the trocar engaged with the cannula. In one embodiment, the bumper 704 is a cylinder and the arcuate surface 710 is the rounded outer surface of the cylinder. A diameter or thickness 716 of the bumper 704 is in a range of about 4 to about 8 millimeters, such as 5 millimeters, for example. The bumper 704 is made from a material which maintains its shape as it is moved over the throat surface of the target subject and is a material that is capable of sliding over the skin surface of the throat surface. In one embodiment, the bumper 704 is made from any suitable rigid or semi-rigid material, including molded plastic, other types of polymers, stainless steel, titanium or cobalt chrome or some combination. In some embodiments, the plate 702 and bumper 704 are made of the same material, and in some embodiments are formed as an integral unit. In some of these embodiments, the plate 702 constitutes a broadened and flattened upper side of the bumper 704 opposite from the surface that settles into recess 640.

Figure 7A:
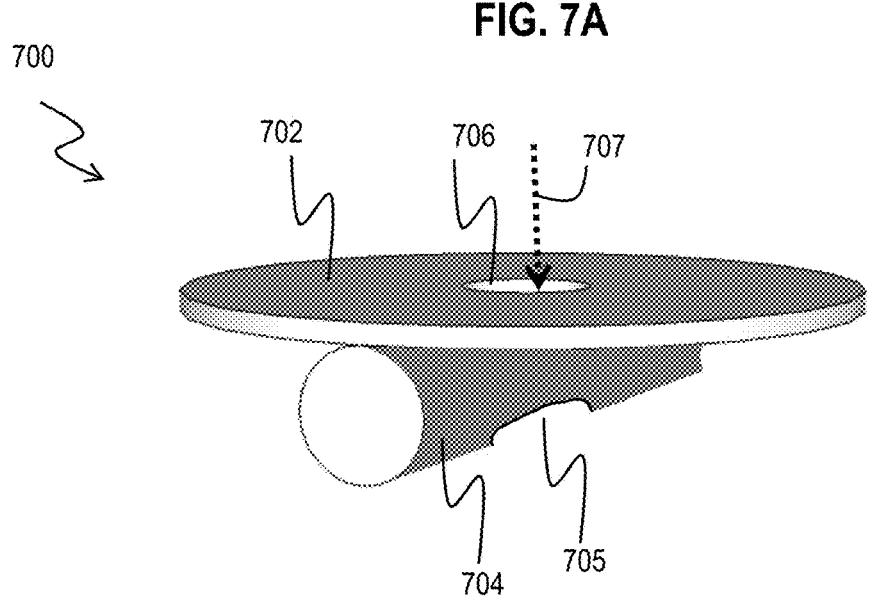
FIG. 7A through FIG. 7D are block diagrams that illustrate an example variation in the system base from that depicted in FIG. 1C and FIG. 4, according to an embodiment.
Figure 7B:
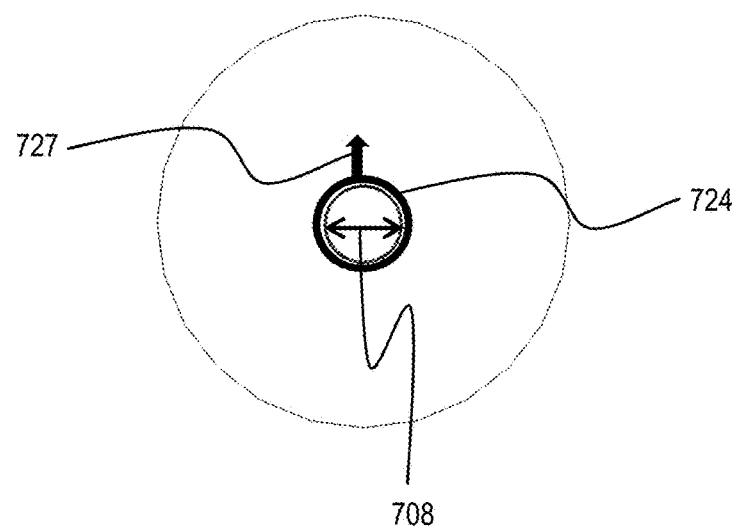
Figure 7C:
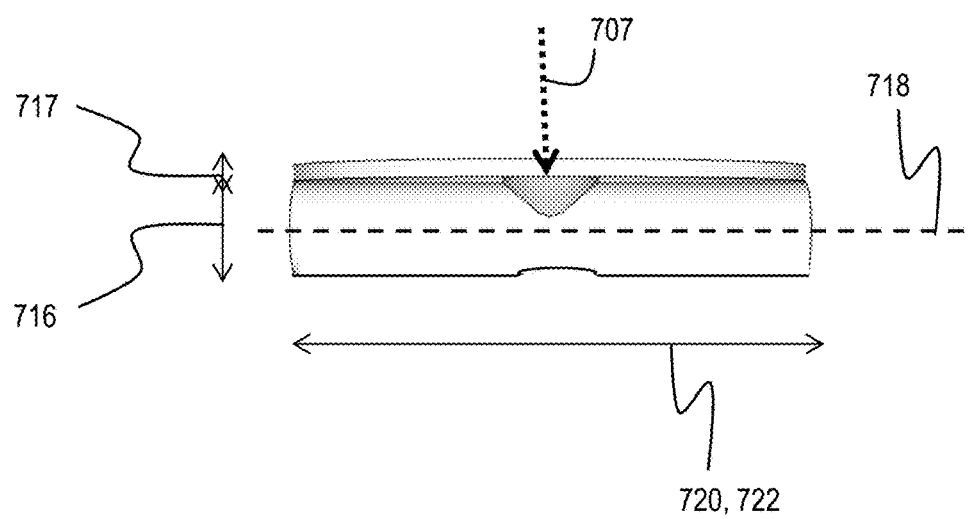
Figure 7D:
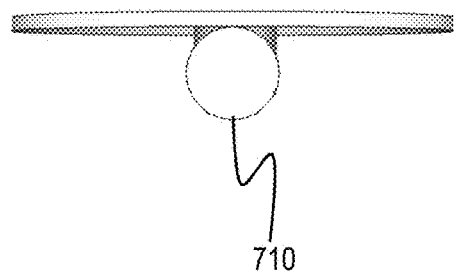

As depicted in FIGS. 7B and 7C, the bumper 704 is oriented such that a longitudinal axis 718 of the bumper is orthogonal to an axis 707 of the system base opening 706 that extends through an opening 705 in the bumper 704. In one embodiment, the opening 705 in the bumper 704 is aligned with the system base opening 706 and has a diameter that is about equal to the diameter 708 of the system base opening 706. As further depicted in FIG. 7C, a length 722 of the bumper 704 is about equal to the diameter or length 720 of the panel 702. In one embodiment, the length 722 of the bumper 704 is in a range of about 5 to about 10 millimeters. Although FIG. 7C depicts that the length 722 of the bumper 704 and the diameter or length 720 of the panel 702 are approximately equal, the length of the bumper may be greater than or less than the length of the panel. In some embodiments, the bumper 704 is configured to rotate relative to the plate 702, so that the bumper can be rolled along the skin into the recess 640.

As depicted in FIG. 7B, in one embodiment of the system base 700, a portion of the panel 702 includes a lighted material 724 that illuminates the system base opening 706 in a dark environment or in an absence of visible light, to assist a user of the system base 700 to locate the system base opening 706 in a dark environment. In another embodiment, a top surface of the panel 702 includes the lighted material 724 or notches, to indicate the orientation of the panel 702 to the user in a dark environment. In one embodiment, the lighted material 724 is a florescent paint that coats a perimeter of the system base opening 706 and is configured to illuminate the perimeter of the system base opening 706 in the visible spectrum, in response to an excitation frequency outside of the visible spectrum, such as infrared (IR) radiation or ultraviolet (UV) radiation, for example. Examples of such fluorescent paints include, but are not limited to, Luminescent Carbon, Fluorescent Silicon, or Low IR emitters such as trivalent chromium. In another embodiment, the lighted material 724 is one or more illumination devices, such as a light emitting diode (LED) that illuminates the system base opening 706. In one example, the illumination device is a low-level infrared emitter that emits infrared radiation in response to a remote control device (not shown), such as at a wavelength in a range between 875 nanometers and 950 nanometers, for example, and a user observes the radiation using low red or infrared goggles. In an additional embodiment, the fluorescent material is a florescent paint that coats an inside surface of the system base opening 706, to illuminate the system base opening 706 in a dark environment. In some embodiments, lighted material 727 is provided on the panel 702, to indicate an orientation of the downward direction of the trachea or a direction of axis 718 of the bumper or both.

To use the system base 700, the bumper 704 is initially positioned with the arcuate surface 710 in contact with the throat surface at a sternal notch (i.e., below the trachea 625 in FIG. 6) or just below the chin (i.e., above the hyoid cartilage 605 in FIG. 6). The bumper 704 is initially oriented such that the longitudinal axis 718 is orthogonal to the throat or torso of the target subject. The bumper 704 is then slid over the skin surface of the throat in a direction of the cricothyroid membrane 630 until the arcuate surface 710 is received in the recess 640 formed by the cricothyroid membrane 630. In one embodiment, the arcuate surface 710 of the bumper 704 is slid along the surface of the throat. In another embodiment, the bumper 704 is rotatable relative to the panel 702 such that the bumper 704 is configured to rotate over the skin surface until the arcuate surface 710 is received within the recess 640.

Figure 8A:
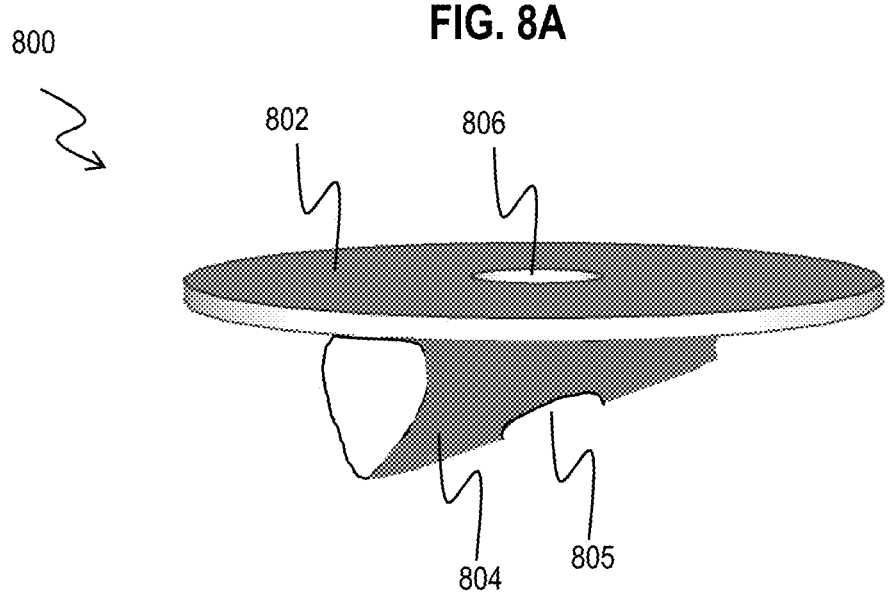
FIG. 8A and FIG. 8B are block diagrams that illustrate another example variation in the system base from that depicted in FIG. 1C, according to an embodiment.
Figure 8B:
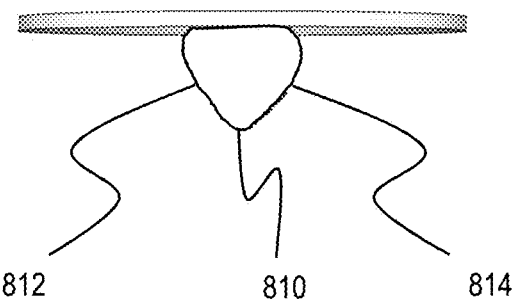

FIG. 8A and FIG. 8B are block diagrams that illustrate a variation in the system base from that depicted in FIG. 1C, according to an embodiment. The system base 800 depicted in FIG. 8A and FIG. 8B is similar to the system base 700 of FIG. 7A through FIG. 7D, with the exception that the bumper 804 has a cross section that is an elongated triangle with rounded edges 810 between adjacent sides 812, 814 of the elongated triangle. In one embodiment, the bumper 804 includes an opening 805 that is aligned with the system base opening 806. The arcuate surface of the bumper 804 that is slid along the throat surface of the target subject is one of the rounded edges 810. In one embodiment, the rounded edges 810 are shaped, based on the depth 650 and the length 660 of the recess 640 formed by the cricothyroid membrane 630. Although FIG. 8A and FIG. 8B depict that the bumper 804 is an elongated triangle with rounded edges, the bumper can be any elongated polygon with any number of sides, provided that the rounded edges of the elongated polygon are shaped to fit in the recess 640 formed by the cricothyroid membrane 630. In some embodiments the upper side of the bumper 804, opposite from the rounded edge 810 formed to contact recess 640, is a broadened and flattened surface to serve as an integrated plate 802.

FIG. 9 is a block diagram that illustrates an example use of the components of FIG. 1A, FIG. 1B, FIG. 1D and FIG. 7A through FIG. 7D, according to an embodiment. A system 900 is provided for emergency apneic oxygenation. The system 900 is similar to the system of FIG. 2A through FIG. 2D, with the exception that the system base 700 has replaced the system base 130. The system 900 includes a cannula 910 that is similar to the cannula 110. The cannula 910 has an inner passage of an inner diameter and a distal portion with a first outer diameter greater than the inner diameter. The cannula 910 is shaped in the distal portion to bend in a first direction 940 along the inner passage. In one embodiment, the distal portion is made of shape memory material. The cannula 910 further includes a cannula base 914 with a second outer diameter greater than the first outer diameter. As illustrated in FIG. 9, the system 900 also includes a trocar 920 configured to engage the cannula 910 by passing through the inner passage and straightening the bent distal portion of the cannula 910. The system base 700 is initially moved along the throat surface 210 until the arcuate surface 710 of the bumper 704 is received within the recess 640 at the cricothyroid membrane 630, as previously discussed. The system base opening 706 and the bumper opening 705 are then aligned with the cricothyroid membrane 630. The engaged trocar 920 and cannula 910 are then inserted through the system base opening 706 and bumper opening 705 and through the throat surface 210 at the cricothyroid membrane 630.

As illustrated in FIG. 9, a portion of a distal end of the trocar 920 is coated with a lighted material 926 configured to illuminate the distal end of the trocar 920 in an absence of visible light. To assist the user inserting the trocar 920 into the system base opening 706 in a dark environment, the lighted material 926 on the distal end of the trocar 920 and the lighted material 724 on the panel 702 illuminate the distal end of the trocar 920 and the system base opening 706. In one embodiment, the lighted material 926 is a fluorescent paint that is used to coat the distal end of the trocar 920. Examples of such fluorescent paints include, but are not limited to, Luminescent Carbon, Fluorescent Silicon, or Low IR emitters such as trivalent chromium. As further illustrated in FIG. 9, a portion of the cannula base 914 is coated with a lighted material 930 configured to illuminate the first direction 940 in an absence of visible light. In one embodiment, when the user inserts the engaged trocar 920 and cannula 910, the user verifies that the illuminated fluorescent material 930 is oriented in the first direction 940 or the downward direction along the airway 220. When the trocar 920 is subsequently removed from the cannula 910, the cannula 910 remains in the airway 220 and the distal portion of the cannula 910 bends in the first direction 940, to accommodate passing a catheter through the cannula and into the airway 220 in the first direction 940 for emergency apneic oxygenation.

As further illustrated in FIG. 9, upon inserting the engaged trocar 920 and cannula 910 through the cricothyroid membrane 630 and into the airway 220 of the target subject, a distance 927 from a distal end of the trocar 920 to a proximal end of the cannula 910 minus a thickness 918 of the cannula base, minus a thickness 717 of the panel 702 and minus a thickness 716 of the bumper 704 is less than a distance from a surface 210 of a throat of the target subject to a distal surface of an airway 220 of the target subject. In one embodiment, the distance 927 depicted in FIG. 9 is longer than the distance 127 depicted in FIG. 2B, by the thickness 716 of the bumper 704. In one embodiment, a distance 929 from the throat surface 210 to a center of the airway 220 is in a range of 19-29 millimeters, such as 24 millimeters, for example. In another embodiment, a diameter 931 of the airway 220 at the cricothyroid membrane 630 is in a range of 18-22 millimeters, such as 20 millimeters, for example.

FIG. 10 is a flow diagram that illustrates an example of a method 1000 for providing emergency apneic oxygenation, according to an embodiment. In step 1001, the arcuate surface 710 of the bumper 704 is moved along the throat surface. As previously discussed, in one embodiment, the arcuate surface 710 initially contacts the throat surface at or near the sternal notch and is moved or rolled superiorly upward toward the cricothyroid membrane 630. In step 1003, upon the arcuate surface 710 sliding over the throat surface and moving into the recess 640 formed by the cricothyroid membrane 630, the arcuate surface 710 is received in the recess 640. In step 1005, when the arcuate surface 710 of the bumper 704 is received in the recess 640, the system base opening 706 is aligned with an entry point in the cricothyroid membrane 630.

In step 1007, the trocar 920 engages the cannula 910 by passing the trocar 920 through the inner passage of the cannula 910. In step 1009, the engaged trocar 920 and cannula 910 are inserted through the system base opening 706 that is aligned with the cricothyroid membrane 630 and pass through the cricothyroid membrane 630 into the airway 220 of the target subject. In some embodiments in which the bumper 704 is rolled into place, the trocar also punctures the bumper 704 to produce an opening through the bumper aligned with the system base opening and the cricothyroid membrane 630. During step 1009, lighted material 926 on a distal end of the trocar 920 and lighted material 724 around the system base opening 706 are used to assist a user inserting the trocar 920 into the system base opening 706 in a dark environment. In step 1011, after the engaged trocar 920 and cannula 910 are inserted into the airway 220, the trocar 920 is rotated to align the trocar and cannula so the cannula will bend downward into the trachea upon removal of the trocar.

In step 1013, the trocar is removed while leaving the cannula 910 inserted at the entry point in the cricothyroid membrane 630 bent in a first direction 940 (i.e. downward direction) along the airway 220. During step 1011, the engaged trocar 920 and cannula 910 are inserted in a manner, so that the distal portion of the cannula 910 is configured to bend in the first direction 940 (i.e. downward direction) along the airway 220 when the trocar 920 is removed in step 1013. In one embodiment, the lighted material 930 on the cannula base 914 is oriented in the first direction 940 during step 1009.

In the foregoing specification, embodiments of the invention has been described with reference to specific examples thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the items, elements or steps modified by the article.

What is claimed is:

1. A kit for emergency apneic oxygenation comprising:
   a cannula comprising
      an inner passage of an inner diameter,
      a distal portion having a first outer diameter greater than the inner diameter, wherein the cannula is shaped in the distal portion to bend in a first direction along the inner passage, and wherein the distal portion is made of shape memory material, and
      a cannula base having a second outer diameter greater than the first outer diameter;
   a trocar configured to engage the cannula by passing through the inner passage and straightening the bent distal portion of the cannula;
   a system base having an opening about equal to the first outer diameter and configured to be placed with the opening centered on an appropriate entry site on a target subject for the trocar engaged with the cannula; and
   a catheter configured to pass through the cannula after insertion of the cannula into the entry site by the engaged trocar and subsequent removal of the trocar, wherein the catheter has a length that is at least a sum of a first distance from the entry site to a sub-segmented bronchus of the target subject and a second distance from the entry site to a supply of fluid.

2. A kit as recited in claim 1, wherein, when the trocar engaged with the cannula is disposed through the system base, a distance from the distal face of the system base to a distal end of the trocar is less than a distance from a surface of a throat of the target subject to a distal surface of an airway of the target subject.

3. A kit as recited in claim 1, wherein the fluid is oxygen.

4. A kit as recited in claim 1, wherein the catheter is divided into a plurality of lumen.

5. A kit as recited in claim 1, wherein the catheter is one of a plurality of catheters encompassed by a sheath, and the inner diameter of the cannula is not less than a diameter of the sheath.

6. A kit as recited in claim 5, wherein corresponding distal ends of the plurality of catheters are configured to be separated to each enter a corresponding sub-segmented bronchus when the cannula is deployed in the airway of the target subject and the sheath is configured through the inner passage of the cannula.

7. A system for emergency apneic oxygenation comprising:
   a cannula comprising
      an inner passage of an inner diameter; and
      a distal portion having a first outer diameter greater than the inner diameter;
   a trocar configured to engage the cannula by passing through the inner passage; and
   a system base comprising
      a panel including a system base opening that has a diameter about equal to the first outer diameter; and
      a cylinder with an outer surface shaped to be received by a recess formed by a cricothyroid membrane between a thyroid cartilage and a cricoid cartilage of a target subject so that the system base opening is centered on the cricothyroid membrane to provide an entry point for the trocar engaged with the cannula.

8. A system as recited in claim 7, wherein a thickness of the cylinder is in a range of 4-8 millimeters.

9. A system as recited in claim 7, wherein at least a portion of the panel is coated with a lighted material configured to illuminate the system base opening in an absence of visible light.

10. A system as recited in claim 7, wherein at least a portion of a distal end of the trocar is coated with a lighted material configured to illuminate the distal end of the trocar in an absence of visible light.

11. A system as recited in claim 7, wherein a light emitting diode (LED) is positioned on at least a portion of the panel to illuminate the system base opening.

12. A system for emergency apneic oxygenation comprising:
   a cannula comprising
      an inner passage of an inner diameter; and
      a distal portion having a first outer diameter greater than the inner diameter;
   a trocar configured to engage the cannula by passing through the inner passage; and
   a system base comprising
      a panel including a system base opening that has a diameter about equal to the first outer diameter; and
      a bumper with an arcuate surface shaped to be received by a recess formed by a cricothyroid membrane between a thyroid cartilage and a cricoid cartilage of a target subject so that the system base opening is centered on the cricothyroid membrane to provide an entry point for the trocar engaged with the cannula;
      wherein the bumper is an elongated polygon comprising rounded edges between adjacent sides of the elongated polygon, and wherein the arcuate surface is one of the rounded edges.

13. A system as recited in claim 8, wherein the elongated polygon is an elongated triangle with rounded edges.

14. A system for emergency apneic oxygenation comprising:
   a cannula comprising
      an inner passage of an inner diameter; and
      a distal portion having a first outer diameter greater than the inner diameter;
   a trocar configured to engage the cannula by passing through the inner passage; and
   a system base comprising
      a panel including a system base opening that has a diameter about equal to the first outer diameter; and
      a bumper with an arcuate surface shaped to be received by a recess formed by a cricothyroid membrane between a thyroid cartilage and a cricoid cartilage of a target subject so that the system base opening is centered on the cricothyroid membrane to provide an entry point for the trocar engaged with the cannula;
      wherein the bumper is oriented such that a longitudinal axis of the bumper is orthogonal to an axis of the system base opening, and wherein a length of the bumper is about equal to a length of the panel.

15. A system for emergency apneic oxygenation comprising:
   a cannula comprising
      an inner passage of an inner diameter,
      a distal portion having a first outer diameter greater than the inner diameter, and
      a cannula base having a second outer diameter greater than the first outer diameter;

a trocar configured to engage the cannula by passing through the inner passage; and a system base including a system base opening that has a diameter about equal to the first outer diameter, wherein at least a portion of the system base is coated with a lighted material configured to illuminate the system base opening in an absence of visible light, and wherein the system base is configured to be placed with the system base opening centered on an entry point on a target subject for the trocar engaged with the cannula, wherein the system base comprises;

a panel including the system base opening, and a cylinder with an outer surface shaped be received by a recess formed by a cricothyroid membrane between a thyroid cartilage and a cricoid cartilage of the target subject so that the system base opening is centered on the cricothyroid membrane to provide the entry point for the trocar.

16. A system as recited in claim 15, wherein the cylinder is rotatable relative to the panel such that the bumper is configured to rotate over one of the thyroid cartilage and the cricoid cartilage and be received in the recess formed by the cricothyroid membrane.

17. A system as recited in claim 15, wherein upon positioning the trocar through the system base opening, a distance from a distal end of the trocar to a proximal end of the cannula minus a thickness of the cannula base, minus a thickness of the panel and minus a thickness of the cylinder is less than a distance from a surface of a throat of the target subject to a distal surface of an airway of the target subject.

18. A system as recited in claim 15, wherein at least a portion of the cannula base is coated with a lighted material configured to illuminate the first direction in an absence of visible light.

* * * * *